United States Patent
Kleinberg et al.

(10) Patent No.: US 9,555,057 B2
(45) Date of Patent: Jan. 31, 2017

(54) COMPOSITIONS AND METHODS FOR REDUCING CUTANEOUS MICROBIOME MALODOR

(71) Applicant: The Research Foundation for The State University of New York, Albany, NY (US)

(72) Inventors: Israel Kleinberg, Smithtown, NY (US); Zegong Zhang, Stony Brook, NY (US)

(73) Assignee: The Research Foundation for The State University of New York, Albany, NY (US)

(*) Notice: Subject to any disclaimer, the term of this patent is extended or adjusted under 35 U.S.C. 154(b) by 0 days.

(21) Appl. No.: 14/869,738

(22) Filed: Sep. 29, 2015

(65) Prior Publication Data

US 2016/0089315 A1    Mar. 31, 2016

Related U.S. Application Data

(60) Provisional application No. 62/057,040, filed on Sep. 29, 2014, provisional application No. 62/116,082, filed on Feb. 13, 2015.

(51) Int. Cl.
| | |
|---|---|
| *A61K 8/27* | (2006.01) |
| *A61K 8/00* | (2006.01) |
| *A61K 33/32* | (2006.01) |
| *A61K 31/315* | (2006.01) |
| *A61K 33/30* | (2006.01) |

(Continued)

(52) U.S. Cl.
CPC .............. *A61K 33/30* (2013.01); *A61K 8/27* (2013.01); *A61K 8/44* (2013.01); *A61K 9/0014* (2013.01); *A61K 31/198* (2013.01); *A61Q 15/00* (2013.01); *A61K 2800/592* (2013.01)

(58) Field of Classification Search
None
See application file for complete search history.

(56) References Cited

U.S. PATENT DOCUMENTS

| | | | | |
|---|---|---|---|---|
| 3,939,261 | A | * | 2/1976 | Barth ................ A61K 8/362 424/49 |
| 4,089,942 | A | | 5/1978 | Boré et al. |

(Continued)

FOREIGN PATENT DOCUMENTS

| | | |
|---|---|---|
| WO | 2009/100281 | 8/2009 |
| WO | 2011/073440 | 6/2011 |

(Continued)

OTHER PUBLICATIONS

International Search Report and Written Opinion for International Application No. PCT/US2015/053015 dated Dec. 14, 2015.

(Continued)

*Primary Examiner* — Jeffrey T Palenik
(74) *Attorney, Agent, or Firm* — Fish & Richardson P.C.

(57) ABSTRACT

A deodorant composition comprising arginine, bicarbonate, zinc and carbonate, preferably arginine bicarbonate and zinc carbonate (ABZC), and one or more physiologically acceptable excipients, administered for the modification of cutaneous microfloras—generally to reduce axillary odor, promote the growth of *Staphylococcus epidermidis* bacteria, inhibit the growth of *Corynebacterium striatum* bacteria, or any or all of the preceding.

20 Claims, 29 Drawing Sheets

(51) Int. Cl.
A61K 8/44 (2006.01)
A61Q 15/00 (2006.01)
A61K 9/00 (2006.01)
A61K 31/198 (2006.01)

(56) References Cited

U.S. PATENT DOCUMENTS

| | | | |
|---|---|---|---|
| 4,565,693 | A | 1/1986 | Marschner |
| 4,634,588 | A | 1/1987 | Moroe |
| 4,708,863 | A | 11/1987 | Bews et al. |
| 5,696,169 | A | 12/1997 | Otsu et al. |
| 5,824,663 | A | 10/1998 | Brockett et al. |
| 6,221,340 | B1* | 4/2001 | Yu ............... A61K 8/22 424/49 |
| 6,239,088 | B1 | 5/2001 | George et al. |
| 8,557,228 | B2 | 10/2013 | Fitzgerald et al. |
| 2009/0202454 | A1* | 8/2009 | Prencipe ......... A61K 8/19 424/52 |
| 2010/0322986 | A1 | 12/2010 | Prencipe |
| 2011/0033409 | A1 | 2/2011 | Tanaka et al. |
| 2011/0200545 | A1 | 8/2011 | Maniga |
| 2013/0331384 | A1 | 12/2013 | Gallo et al. |

FOREIGN PATENT DOCUMENTS

| | | |
|---|---|---|
| WO | 2014/098813 | 6/2014 |
| WO | 2015/094254 | 6/2015 |

OTHER PUBLICATIONS

Bauer et al., "Antibiotic Susceptibility Testing by a Standardized Single Disk Method", The American Journal of Clinical Pathology, 45(4):493-496 (1966).

Chen et al., "Evolving Epidemiology of Pediatric *Staphylococcus aureus* Cutaneous Infections in a Baltimore Hospital", Pediatric Emergency Care, Lippincott Williams & Wilkins, 22(10):717-723 (2006).

David and Daum, "Community-Associated Methicillin-Resistant *Staphylococcus aureus*: Epidemiology and Clinical Consequences of an Emerging Epidemic", Clin. Microb. Reviews p. 616-687 (2010).

Denepitiya and Kleinberg, "A Comparison of the Acid-Base and Aciduric Properties of Various Serotypes of the Bacterium *Streptococcus mutans* Associated with Dental Plaque", Archs Oral Biol. 29(5):385-393 (1984).

Denepitiya and Kleinberg, "A Comparison of the Microbial Compositions of Pooled Human Dental Plaque and Salivary Sediment", Archs oral Biol. (27):739-745 (1982).

Emter and Natsch, "The Sequential Action of a Dipeptidase and a β-Lyase Is Required for the Release of the Human Body Odorant 3-Methyl-3-sulfanylhexan-1-ol from a Secreted Cys-Gly-(S) Conjugate by *Corynebacteria*", J. of Biol. Chem. 283(30):20645-20655 (2008).

Frank et al., "The Human Nasal Microbiota and *Staphylocccus aureus* Carriage", PLoS ONE, www.plosone.org; 5(5):e10598 (2010).

French, "Methods for screening for methicillin-resistant *Staphyloccus aureus* carriage", The Author, Journal Compilation © The Author European Society of Clinical Microbiology and Infectious Diseases, 15(Supp17): 10-16 (2009).

Han et al., "Evaluation of mannitol sugar agar, CHROMagar *Staph aureus* and CHROMagar MRSA for detection of methicillin-resistant *Staphylocccus aureus* from nasal swab specimens", J. of Medical Microbiology, 56:43-46 (2007).

Jackman, "Body Odor—The Role of Skin Bacteria", Seminars in Dermatology 1(2):143-148 (1982).

Kleinberg and Codipilly. "Modeling of the oral malodor system and methods of analysis", Quinlessence International, 30:357-369 (1999).

Kleinberg and Codipilly, "Cysteine challenge testing:a powerful tool for examining oral malodour processes and treatments in vivo", International Dental Journal 52:221-228 (2002).

Kleinberg and Codipilly, "$H_2S$ generation and $E_h$ reduction in cysteine challenge testing as a means of determining the potential of test products and treatments for inhibiting oral malodor", J. Breath Res. 2: 1-9 (2008).

Klevens et al., "Invasive Methicillin-Resistant *Staphylococcus aureus* Infections in the Unites States", JAMA 298(15):1763-1771 (2007).

Leyden et al., "The Microbiology of the Human Axilla and Its Relationship to Axillary Odor, The Journal of Investigative Dermatology" 77:413-416 (1981).

Leyden and McGinley, "Coryneform bacteria", p. 102-115 (1993).

Mainous et al., "Nasal Carriage of *Staphylococcus aureus* and Methicillin-Resistant *S aureus* in the United States, 2001-2002", Ann. Fam. Med. 4:132-137 (2006).

Nakatsuji et al., "Skin commensal bacteria acts as antimicrobial shield: Identification of . . . *Staphylococcus epidermis*", Immunology 2: Innate Immunity & Microbiology /Abstracts; Abstract # 642 (2012).

Noble, "Staphylococci on the skin", The Skin of Microfolora and Microbial Skin Disease, Cambridge University Press, p. 135-152 (1993).

Pader, Oral Hygiene products and practice/ Health Sciences Library Book Collection, New York: Dekker (1988).

Peacock et al., "What determines nasal carriage of *Staphylococcus aureus*?", Trends in Microbiology 9(12):605-610 (2001).

Public Health Dispatch: Outbreaks of Community-Associated Methicillin Resistant *Staphylococcus aureus* Skin Infections—Los Angeles County, California, 2002-2003; hitp://www.cdc.gov/mmwr/preview/mmwrhtml/mm5205a4.htm Oct. 5, 2015.

Sandham and Kleinberg, "Effect of Glucose Concentration on Carbon Dioxide Production in a Human Salivary Sediment System", Archs oral Biol., 15:1285-1301 (1970).

Shehadeh et al., The Bacteria Responsible for Axillary Odor, II, J. Invest. Dermatol. 41:3-3 (1963).

Starkenmann et al., "Identification of the Precursor of (S)-3-Methyl-3-sulfanylhexan-l-ol, the Sulfury Malodour of Human Axilla Sweat", Chemistry and Biodiversity 2:705-716 (2005).

Taylor et al., "Characterization of the microflora of the human axilla", International Journal of Cosmetic Science 25:137-145 (2003).

Trocazz et al., "3-Methyl-3-sulfanylhexan-1-ol as a Major Descriptor for the Human Axilla-Sweat Odour Profile", Chemistry & Biodiversity 1:1022-1035 (2004).

Uehara et al, "Bacterial Interference among nasal inhabitants: eradication of *Staphylococcus aureus* from nasal cavities by artificial implantation of *Corynebacterium* sp.", J. of Hospital Infection 44:127-133 (2000).

Wertheim et al., "The role of nasal carriage in *Staphylococcus aureus* infections", The Lancet Infectious Diseases, 5:751-762 (2005).

Wueyeweera and Kleinberg, "Acid-Base pH Curves In Vitro with Mixtures of Pure Cultures of Human Oral Microorganisms", Archs oral Biol. 34(1):55-64 (1989).

Zeng et al., "Analysis of Characteristic Odors From Human Male Axillae", J. of Chem. Ecology 17(7):1469-1493 (1991).

* cited by examiner

Foot odor: (F-0 to 4), Vinegar odor: (V-0 to 4), Foot & Vinegar odor: (F/V-0 to 4).
0 to 4: odor intensity from 0 to 4

*Zinc salt buffers include zinc citrate at pH 4.0, zinc chloride at pH 5.0, zinc acetate at pH 6.0, zinc lactate at pH 7.0 and zinc carbonate at pH 8.0.

*Zinc salt buffers include zinc citrate at pH 4.0, zinc chloride at pH 5.0, zinc acetate at pH 6.0, zinc lactate at pH 7.0 and zinc carbonate at pH 8.0.

*The Density of colonies: scales (0-10) of the number of colony on plate: 0 - no colony, 1 - < 10, 2 – 10 to 20, 3 – 20 to 30, 4 – 30 to 50, 5 – 50 to 100, 6 – 100 to 200, 7 – 250 to 500, 8 > 500, 0 – colonies merge and almost form a layer and are unable to count, 10 – colonies form a layer.

*The Density of colonies: scales (0-10) of the number of colony on plate: 0 - no colony, 1 - < 10, 2 – 10 to 20, 3 – 20 to 30, 4 – 30 to 50, 5 – 50 to 100, 6 – 100 to 200, 7 – 250 to 500, 8 > 500, 9 – colonies merge and almost form a layer and are unable to count, 10 – colonies form a layer.

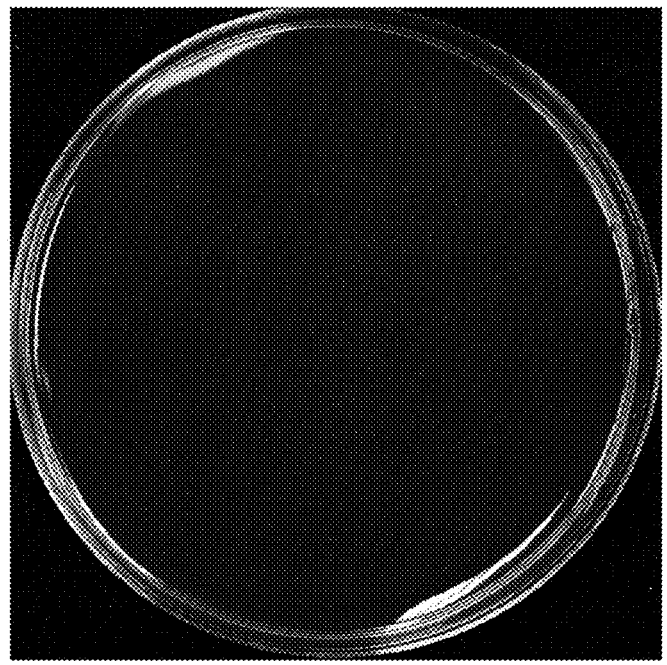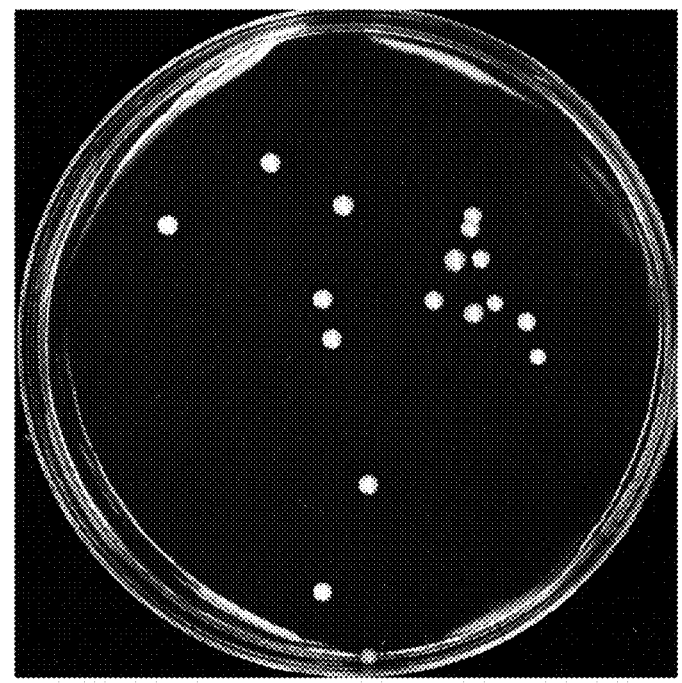
FIG. 28

COMPOSITIONS AND METHODS FOR REDUCING CUTANEOUS MICROBIOME MALODOR

FIELD OF THE INVENTION

The present invention relates to deodorant compositions and more particularly to compositions for reducing cutaneous malodor, including axillary malodor.

BACKGROUND OF THE INVENTION

The human axilla (i.e., underarm) is a region of the human body that contains a high density of apocrine glands that produce and secrete sweat, as occurs during increased physical activity or exposure to heat. Also, it has been known for many years that sweat (or perspiration) per se contains odorless precursors which, when acted upon by the axillary bacteria, produce sugars, sugar amines, amino acids, and short chain carboxylic acids (SCCAs), of which some are degraded further to products that include odorants that are associated to a major extent with axillary odor (Zeng et al, 1991; Jackman, 1982).

The axillary microbiome in humans includes a variety of microorganisms, of which staphylococci, corynebacteria and propionibacteria are among the most prominent (Starkemann et al., 2005, Troccaz et al., 2004, Jackman, 1982). A study of 229 subjects by Leyden et al. (1981) established that axillary odor typically includes a strong pungent and a weak secondary odor, that is acidic and generally of lesser intensity. Leyden et al. further found that the primary axillary bacteria responsible for the strong pungent odor were corynebacteria. More recently, Emter et al. (2008) narrowed this finding to specific species among the corynebacteria. Leyden et al. (2002) demonstrated that staphylococci and other axillary bacteria also contribute to axillary odor. The contributions of these other (non-corynebacteria) bacteria to the odor bouquet are products that tend to be more acidic and less offensive in nature. What was not known was whether and/or how these two major odor streams might be related and if and how they could both be inhibited simultaneously. Such interaction and balancing are central to manipulating and modifying microfloras found in the oral cavity (Kleinberg et al., 2002), and possibly also in the vagina and large intestine. Such modification at these sites provide a more healthy condition, which may be termed dysbiotic to eubiotic microflora transformation.

SUMMARY OF THE INVENTION

To investigate whether such interaction and balancing exists in the axillary context, and if so, whether such interaction and balancing could be modulated, an approach initially developed for examining the metabolic contribution of the main microbial components of another and even more complex microbiome, the oral cavity (Kleinberg et al., 2002) was adapted to characterize the bacterial components generally responsible for the development of human axillary odor. Accordingly, a metabolic survey was carried out to identify and assess the relation between (i) the malodor metabolism of the axillary microbiome and (ii) its microbial composition. The basic information obtained was then utilized to assess the main substrates and factors that facilitate and inhibit production of their axillary odoriferous products.

Interestingly, malodor produced in foot (or toe) web sites (i.e., foot odor) shows significant similarity to that of axillary odor. Thus, except where otherwise noted, "axillary odor" and "foot odor" are used interchangeably herein. The investigation and approach to understanding the formation of odor at these two sites (axilla and toe-web) involved five areas of exploration. Example I consisted of a survey to determine, from among the prominent members of the human axillary microflora, which bacteria have the ability to utilize, from amongst a wide range of substrates, those primarily responsible for the metabolic activities that characterize the odor generating and odor inhibiting abilities of the axillary microbiome. Example II examined the effects of zinc and arginine on their ability to affect the sulfurous odor generated from cysteine (see, e.g., Kleinberg et al., 2002 and 2008) and foot-web odor produced from leucine and isoleucine. Surprisingly, one amino acid, phenylalanine, was also found to be a producer of a pleasant rather than an unpleasant odor product and was thus employed in the development of a desirable further anti-odor composition.

Example III examined the role of pH on the odor production processes observed in Part II, since it was suspected that short chain fatty acids were involved therein and that these acids and their pH could be determinants of odorant volatility and nasal detection.

Example IV examined the effects of various arginine bicarbonate/zinc carbonate (ABZC) combinations on odor generation.

Example V examined elements, particularly pH regulation, to identify methods and compositions for favoring relative growth of desirable microorganisms over undesirable bacteria to reduce malodor.

The present invention is directed to a topical deodorant composition including arginine or its salt, a zinc salt, and, optionally, a buffer for maintaining the pH of the composition at 6.0 or greater.

BRIEF DESCRIPTION OF THE DRAWINGS

The invention will be more fully understood from the following detailed description taken in conjunction with the accompanying figures, in which:

FIG. 23, FIG. 24 and FIG. 25-28 show the effect of 12.0 mM arginine bicarbonate on growth of an 8.3% (v/v) 1:1 mixture of *Corynebacterium striatum* and *Staphylococcus epidermidis* incubated with 12.0 mM zinc carbonate and 6.0 mM CIL, with or without 12.0 mM arginine bicarbonate, at 37° C. for 0 (FIG. 25), 24 (FIG. 26), 48 (FIG. 27) or 72 (FIG. 28) hours.

DETAILED DESCRIPTION OF THE INVENTION

Figure 1:
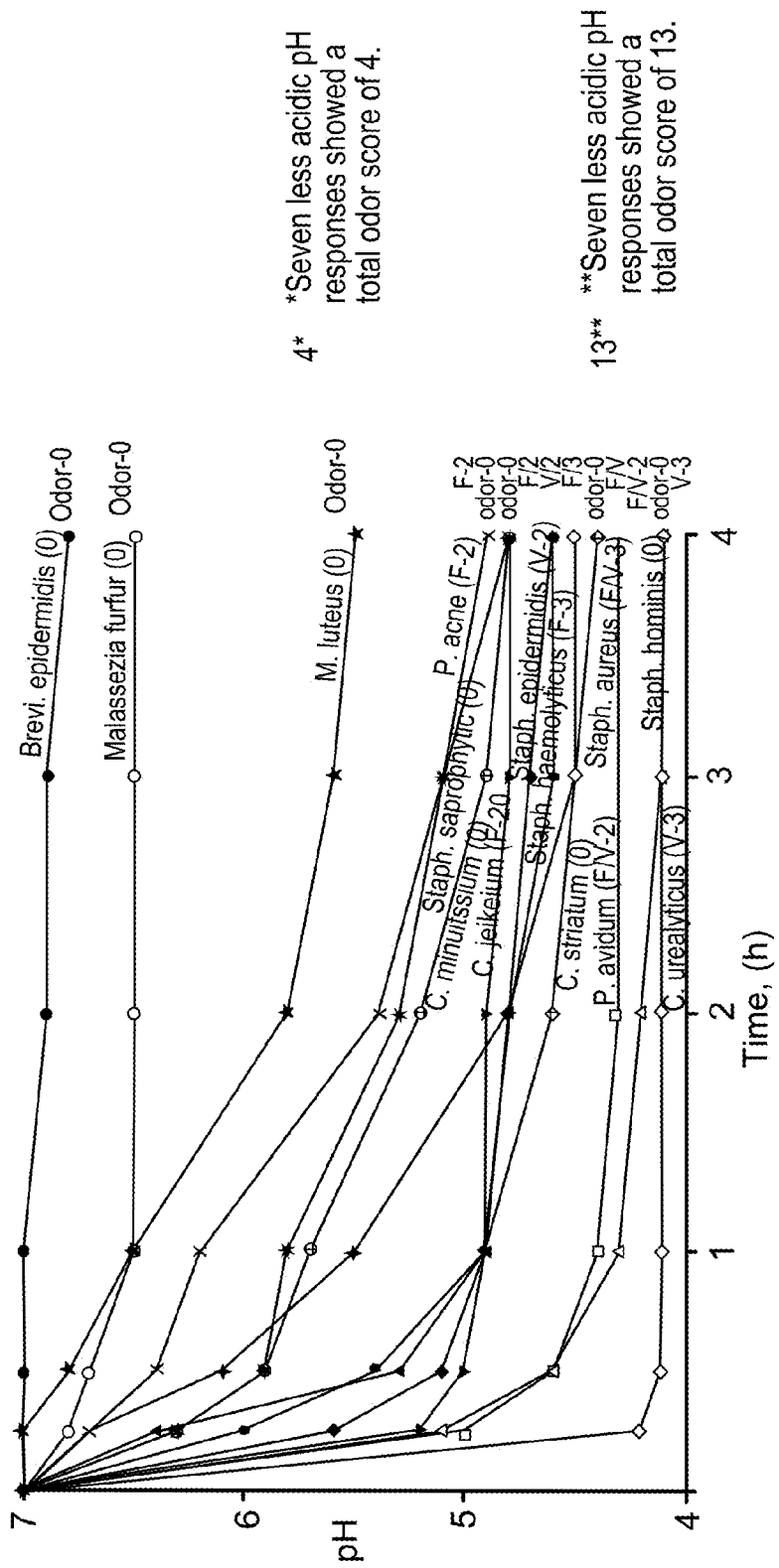
FIG. 1 is a graph showing the pH and odor responses of axillary microflora bacteria to 28 mM glucose.

The survey of bacteria and substrates undertaken according to the present invention to identify the dominant bacteria involved in axillary or foot web odor formation and their primary substrates confirmed that corynebacteria, staphylococci and proprionibacteria are the main microorganisms involved in axillary body odor. The present invention demonstrates that with *Staph. epidermidis*, *C. striatum* and *P. avidum* as prominent representative bacteria, the odor arising from *C. striatum* is pungent and objectionable, while the odor arising from *Staph. epidermidis* is that of vinegar and foot odor-like and only objectionable at acidic pH. Odor from *P. avidum* is contributive (i.e., additive). Activity at acidic pH but not at neutral or alkaline pH is consistent with the presence of low molecular weight fatty acids. It was also found that a sulfurous odor is produced from cysteine, an observation not previously reported. Such odor would arise from hydrogen sulfide, which is produced to varying degrees in numerous bacteria.

The present invention has demonstrated that the unpleasant odors arising in individuals suffering from axillary odor stem mainly from the presence of certain amino acids found in sweat. Besides cysteine and its resulting sulfurous odor, leucine and isoleucine yield odors consistent with those from several short chain carboxylic acids (SCCAs). All three of these amino acids are major odor-producing substrates for *C. striatum* and, accordingly, generators of common human body malodor. Presumably, the vinegar-like odor comes from acetic acid and the more objectionable, foot-web odor from other short chain carboxylic acids, namely isovaleric and propionic acids. Cysteine, upon degradation yields the sulfurous smelling hydrogen sulfide; leucine yields isovaleric and acetic acids and isoleucine yields propionic acid.

At the same time that microbial metabolism produces $H_2S$, $HS^-$ is also generated, which is primary to the lowering of the $E_h$ (Kleinberg et al., 2008). This is key to the putrefaction process, under which protein and amino acid degradation occur. This process involves the amino acids leucine and isoleucine, which as indicated above, would account for the vinegar (viz. acetic acid) and foot-web odor (viz. isovaleric acid). Preparation of mixtures of short chain carboxylic acids (SCCAs) gave odors consistent with these conclusions.

It has been discovered by the present inventors that deodorant compositions containing zinc and arginine compounds are effective for inhibiting axillary and foot-web odor. More particularly, it has been found that compositions containing zinc carbonate and arginine bicarbonate (ABZC) are effective for inhibiting axillary and foot-web odor. Zinc ion in the formulation inhibits cysteine utilization and hence inhibits the generation of the sulfurous odor. By ensuring that the pH is not acidic, short chain carboxylic acids are ionized and are hence not volatile and are not released into the air. Thus, detectable odor is minimized. Similarly, the degradation products of leucine and isoleucine, which lead to short chain amino acids, are also not released into the air. The presence of carbonate and bicarbonate ensures a stable alkaline pH.

From the detection of acidic odor, it is evident that short chain fatty acids (SCCAs) are an important element in malodor. From this, it is also evident that the acidic form of short chain fatty acids is key to their volatility, whereas their base forms are not. An acidic pH would produce the volatile form, whereas a higher pH would not. Accordingly, a pH near or above neutrality is desirable. Such a pH is achieved through proper anion selection. In this case, the carbonate anion was found to be appropriate. Combined with zinc as zinc carbonate, this gave an optimal and stable pH.

It was discovered that phenylalanine provides a pleasant odor upon degradation by *C. striatum*. This odor is reminiscent of the young, both humans and many household pets.

Thus, the main metabolic elements influencing axillary malodor generation have now been identified. Firstly, cysteine catabolism is of central importance in axillary malodor generation, because upon its degradation by several of the axillary bacteria, $H_2S$ with its sulfurous odor, is generated. Such cysteine catabolism is inhibited by zinc ion in an embodiment of the present invention. *C. striatum*, a central microorganism in malodor generation, degrades leucine and isoleucine and produces therefrom short chain carboxylic acids that are odorous. Leucine is degraded to pungent isovaleric acid; isoleucine degradation results in the formation of acetic and propionic acids. All three are short chain carboxylic acids, and are hence volatile below but not above pH 6.0. Thus, if a topical formulation provides a pH greater than 6.0, little or no malodor from this source will be perceived. To achieve and sustain the pH needed, arginine as bicarbonate is included in the composition. When arginine bicarbonate is combined with zinc carbonate, a stable inhibitory pH is produced, which ensures no release of the short chain carboxylic acids including pungent, isovaleric acid. The formulation also favors, because of its zinc component, a higher $E_h$. Associated therewith, are reduced putrefaction and lower generation of $H_2S$ and sulfurous odor.

Deodorant compositions as described herein are administered, preferably topically, for the treatment of any one or more symptoms desirable of change, e.g., cutaneous (including axillary) malodor. Dosage forms are solid or free-flowing. Dosage forms include, but are not limited to, soaps, sprays, drops, aerosols, powders, roll-ons, lotions, creams, sticks, solutions, sachets, colloidal suspensions, films, patches and ointments.

Deodorant composition as described herein may have a pH of at least 6.0, or at least 7.0, or at least 8.0, or at least 9.0 upon topical administration.

Deodorant compositions as described herein may optionally include one or more physiologically acceptable buffers sufficient to maintain the pH of said composition, e.g., at 6.0 or greater, at 7.0 or greater, at 8.0 or greater, or at 9.0 or greater upon topical application. Such buffers are generally known in the art, and may include, e.g., ACES, acetic acid, ADA, AMP, AMPD, bicine, bis-Tris, bis-Tris propane, BES, boric acid, cacodylate, CABS, CAPS, CAPSO, CHES, citric acid, diethanolamine, DIPSO, EPPS/HEPPS, ethanolamine, formic acid, glycine, glycylglycine, HEPES, HEPPSO, histidine, imidazole, lactic acid, maleic acid, malic acid, MES, MOPS, MOPSO, morpholine, phosphate, phosphoric acid, picolinic acid, PIPES, piperazine, piperidine, pivalic acid, POPSO, pyridine, succinic acid, TAPS, TAPSO, TEA, TES, tricine, and/or Tris.

Except where otherwise noted, the terms "microbiome," "microbiota," and "microflora" are used interchangeably herein, the terms "foot," "foot web," "foot-web," "toe," "toe web" and "toe-web" are used interchangeably herein, the terms "fatty acid," "carboxylic acid," "short chain fatty acid," "short chain carboxylic acid," and "SCCA" are used interchangeably herein, and the terms "odor" and "malodor" are used interchangeably herein as well.

The terms "cutaneous" and "skin" refer, in the context of the present invention, to regions of the human body including, e.g., the axilla, foot-webs and nasal atrium.

The terms "physiologically acceptable" and "physiologically-acceptable" denote, in the context of the present invention, "safe and effective when administered to humans and/or mammals in need thereof," e.g., to reduce axillary odor, promote the growth of *Staphylococcus epidermidis* bacteria, inhibit the growth of *Corynebacterium striatum* bacteria, or any or all of the preceding entities.

EXAMPLES

The following examples are intended to illustrate, but not limit, the present disclosure.

Example I

Survey of the Human Axillary Microbiome for Ability of its Most Prominent Bacterial Members to Generate Changes in Acid-base (pH), Oxidation-reduction ($E_h$), Malodor and Hydrogen Peroxide Generation Processes, when Incubated Individually with a Wide Range of Carbohydrate and Amino Acid Substrates Materials and Methods
Identification of the Axillary Microorganisms Most Likely to be Involved in Significant Participation in Axillary Odor Generation Pure cultures of the numerically most prominent microorganisms normally resident on human axillary skin (see Table 1) were surveyed for their effects on (i) pH, (ii) $E_h$, (iii) ability to generate malodor and (iv) ability to generate hydrogen peroxide. Four hour incubation experiments were conducted, in which each of a wide range of carbohydrate and amino acid substrates (see Table 1) were surveyed for malodor production and related changes in pH and $E_h$ thereto. The bacteria selected were obtained from the American Type Culture Collection (ATCC; 1080 University Boulevard, Manassas, Va. 20110-2209 USA) and concentrations of these bacteria singly or in combination were prepared as 8.3% (v/v) microbial compositions, as in earlier such studies with oral bacteria (Denepitiya and Kleinberg, 1982 and 1984).

Each microorganism was recovered from its frozen state at −70° C. and grown at 37° C. in 10 ml of appropriate and respective culture media for a period between 24 and 48 hours (see Table 1). Incubations were carried out to middle and late exponential stages of bacterial growth under the incubation conditions indicated in Table 1. A 1.5 ml inoculum was transferred therefrom to polypropylene bottles containing 150 ml of the initial growth medium. This was then incubated at 37° C. for 24 to 48 hours. Bacteria were harvested by centrifugation (DuPone, Sorvall, Newtown, Conn.) at 10,000 g and 4° C. for 20 min. The volume of bacterial pellet obtained was between about 2.5 and 3.5 ml. The sediment was then washed with sterile distilled water to remove residual growth medium. This was done by centrifuging the bacterial sediment three times at 1,740 g for 15 min at 4° C. The resulting sediment was re-suspended in sterile distilled water at a concentration of 25% (v/v) and stored at 4° C. until time of inoculation shortly thereafter on various media (see Table 1 below).

TABLE 1

Microorganisms, culture media and growth conditions for the axillary microorganisms studied

| Name of bacteria and fungus | ATCC# | Cultural medium | Growth conditions |
|---|---|---|---|
| *Corynebacterium striatum* | 43751 | Brain heart infusion | 30-37° C., aerobic |
| *Corynebacterium jeikeium* | BAA-949 | Trypticase soy with 0.1% Tween 80 | 37° C., aerobic |

TABLE 1-continued

Microorganisms, culture media and growth conditions
for the axillary microorganisms studied

| Name of bacteria and fungus | ATCC# | Cultural medium | Growth conditions |
|---|---|---|---|
| Corynebacterium urealyticum | 43042 | Mueller Hinton medium with 10% sterile rabbit serum | 37° C., aerobic |
| Corynebacterium minutissium | 23348 | Brain heart infusion | 37° C., aerobic |
| Brevibacterium epidermidis | 35514 | Brain heart infusion | 37° C., aerobic |
| Staphylococcus epidermidis | 12228 | Brain heart infusion | 37° C., aerobic |
| Staphylococcus hominis | 27844 | Brain heart infusion | 37° C., aerobic |
| Staphylococcus saprophyticum | 15305 | Brain heart infusion | 37° C., aerobic |
| Staphylococcus haemolyticus | 29970 | Brain heart infusion | 37° C., aerobic |
| Staphylococcus aureus | 25923 | Brain heart infusion | 37° C., aerobic |
| Micrococcus luteus | 10773 | Brain heart infusion | 30° C., aerobic |
| Propionibacterium acnes | 6919 | Brain heart infusion | 37° C., anaerobic |
| Propionibacterium avidum | 49754 | Brain heart infusion | 37° C., anaerobic |
| Yeast: Malassezia furfur | 44344 | Pityrosporum media - agar slant, 30° C., aerobic, 72 hours, then transfer to Pityrosporum media - broth, 30° C., aerobic, 72 hours | |

Preparation of Substrate Media for the Metabolic Characterization of Each of the Different Bacteria of the Axillary Microbiome Examined and Studied Herein Stock solutions were prepared that consisted of 50 ml of 84 mM solutions of (i) each of the following carbohydrates: glucose, galactose, fructose, maltose, lactose, sucrose, glucosamine, galactosamine, N-acetyl-D-galactosamine, N-acetyl-D-glucosamine, N-acetyl neuraminic (sialic) acid, fucose and glycogen (each obtained from Sigma-Aldrich, Co., St. Louis, Mo. USA) and (ii) each of the following 21 amino acids: alanine, arginine, asparagine, cysteine, cystine, glutamic acid, glutamine, glycine, histidine, isoleucine, leucine, lysine, methionine, ornithine, phenylalanine, proline, serine, threonine, tryptophan, tyrosine, and valine (each obtained from Sigma-Aldrich, Co., St. Louis, Mo. USA).

Pre-incubation to Deplete Stored Carbohydrate and Other Carbon/energy Sources Acquired During Growth in Culture Each pure culture was pre-incubated at 37° C. at pH 7.0 to exhaust or reduce any stored carbohydrate and other carbon/energy sources acquired during growth in culture. This was essential and was done by holding the pH at 7.0, for about 15 min. using 0.1 M NaOH as titrant in a pH-Stat (Sandham and Kleinberg, 1970).

Thereafter, depletion of stored carbohydrate usually took about 2 hours and completion was evident, when addition of little or no further NaOH addition was necessary. Each microorganism was then washed for a final time with sterile distilled water and re-suspended thereafter in distilled water at a cell concentration of 25.0% (v/v).

Incubation with Each of the Various Carbohydrate and Amino Acid Substrates Surveyed and their Respective Effects on the pH and $E_h$ In a series of experiments, incubation mixtures (900 µl) were prepared, where each contained a pure culture at a suspension concentration of 8.3% (v/v) (i.e. 300 µl of 25% pure culture suspension in 900 µl of the mixture), and a test carbohydrate substrate at a concentration of 28 mM (i.e. 300 µl of 84 mM stock solution in 900 µl of the mixture) or test amino acid at a concentration of 6 mM (i.e. 300 µl of 18 mM stock solution in 900 µl of the mixture) and 300 µl of distilled water. The amino acid stock solutions consisted of 50 ml of 18 mM solutions of each of the following amino acids: alanine, arginine, asparagine, cysteine, cystine, glutamic acid, glutamine, glycine, histidine, isoleucine, leucine, lysine, methionine, ornithine, phenylalanine, proline, serine, threonine, tryptophan, tyrosine, or valine. Each incubation mixture was adjusted to pH 7.0 with 0.1 M NaOH or 0.1 M HCl and resulting mixtures were then incubated in a water bath at 37° C. for 4 hours.

At various times throughout each incubation (0, 0.25, 0.5, 1.0, 2.0, 3.0 and 4.0 hours), (i) the pH was measured with a combined pH and reference electrode (Part no. E16M306; Type pH C3006-9, Radiometer Analytical S.A.S., 69120 Vaulx-en-Velin, France) connected to one of two same pH meters (M26 Radiometer, Copenhagen NV, Denmark) and (ii) the $E_h$ was measured with a platinum wire electrode (Kleinberg et al, 1999) in combination with a "Red Rod" reference electrode (Part no. E21M009, Type Ref 201, Radiometer Analytical S.A.S, 69627 Villeurbanne Cedex, France) and a connecting KCl salt bridge. Both of these electrodes were connected to a second pH meter (pH M26 Radiometer Copenhagen NV, Denmark) and used here as a millivoltmeter. For the $E_h$ measurements, when the $E_h$ electrode was immersed in an incubation mixture, each $E_h$ reading was recorded after allowing several seconds for each reading to stabilize. The $E_h$ value was related to that of the hydrogen electrode by adding to each reading the difference between the $E_0$ value for the Red Rod reference element-mercury and hydrogen electrodes—i.e. 270 my at 25° C.

At each time point, the odor was determined organoleptically by immersing a solid glass rod into each incubation mixture, stirring gently 3 times and then removing and carefully smelling the rod after 5 seconds. The intensity of the odor was assessed on a 0 to 4 numerical scale (0—no odor, 1—mild odor, 2—moderate odor, 3—strong odor, and 4—very strong odor).

Testing for Hydrogen Peroxide Production

This parameter was assessed by placing 5 µl of 16.7% (w/v) catalase (SIGMA Aldrich Corp. St. Louis, Mo. USA) on a glass slide. To this, 5 µl taken from an incubation mixture under test was added to the catalase on the slide, and then mixed with a fine glass rod and checked for release of tiny bubbles. These would be oxygen bubbles produced, if hydrogen peroxide on a slide is present and hydrolyzed by the catalase enzyme. Scoring was done on an intensity scale of 0-5.

Figure 2:
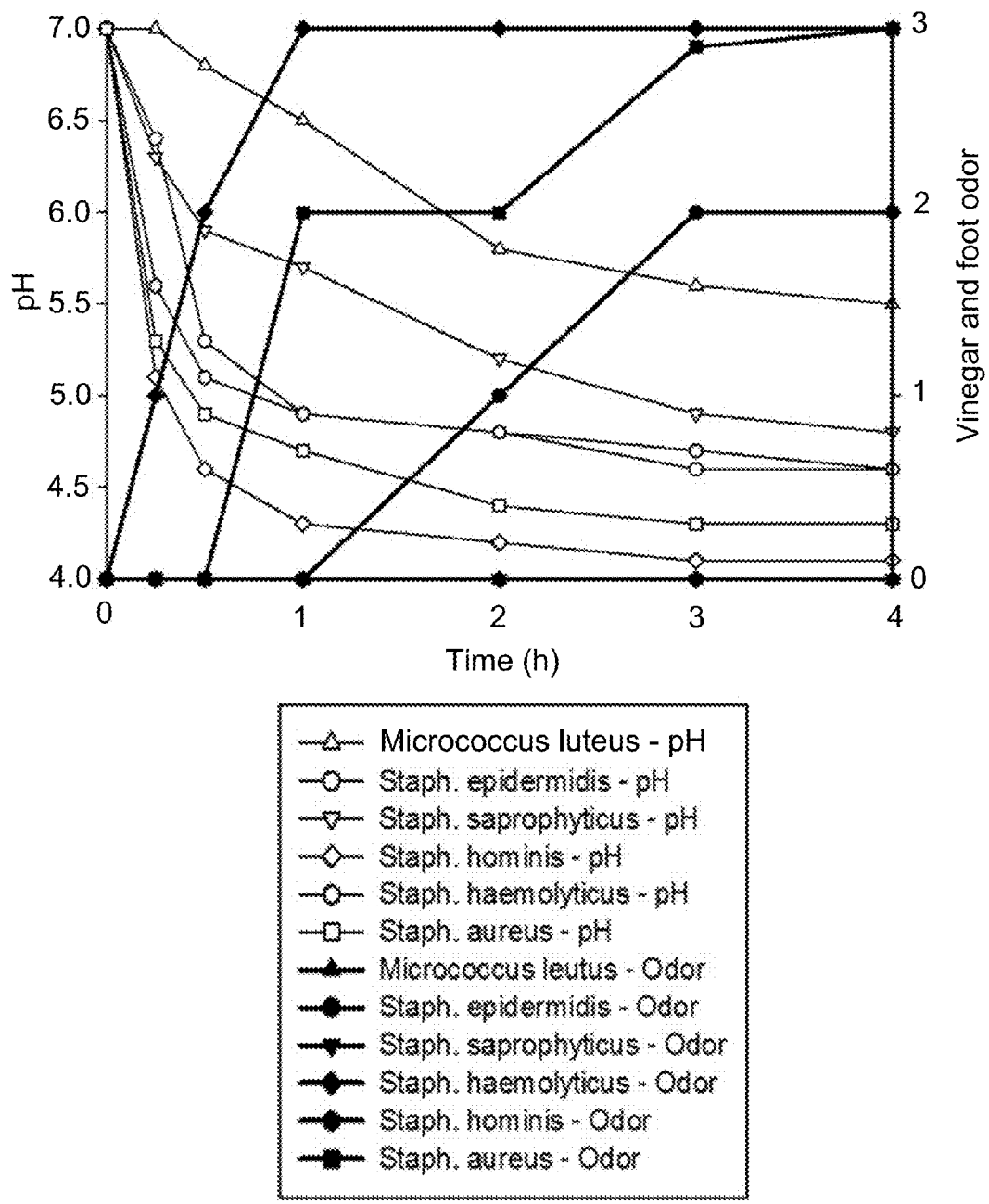
FIG. 2 is a graph showing the pH and odor responses of *Staphylococci* and *Micrococcus luteus* to 28 mM glucose.
Figure 3:
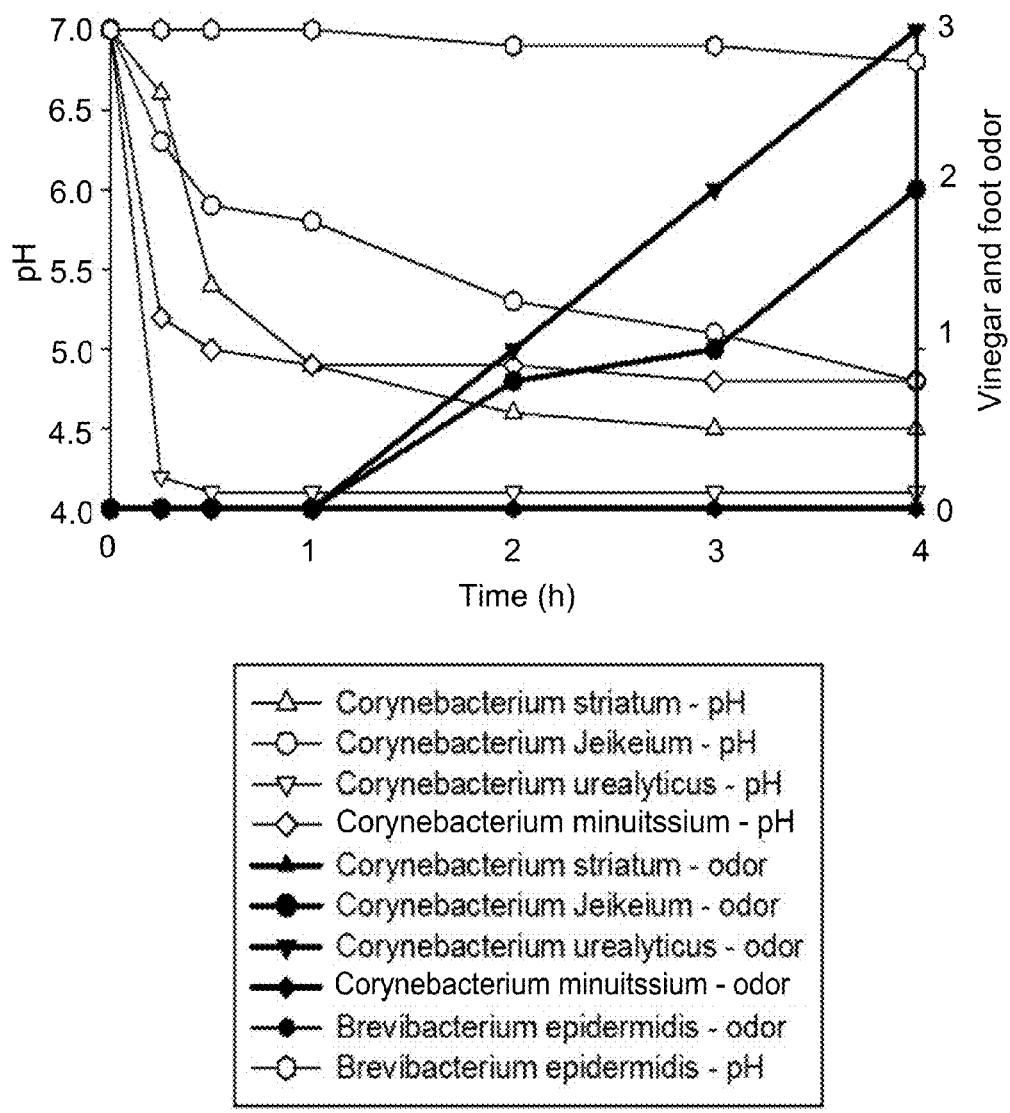
FIG. 3 is a graph showing the pH and odor responses of *Corynebacteria* and *Brevibacterium epidermidis* to 28 mM glucose.
Figure 4:
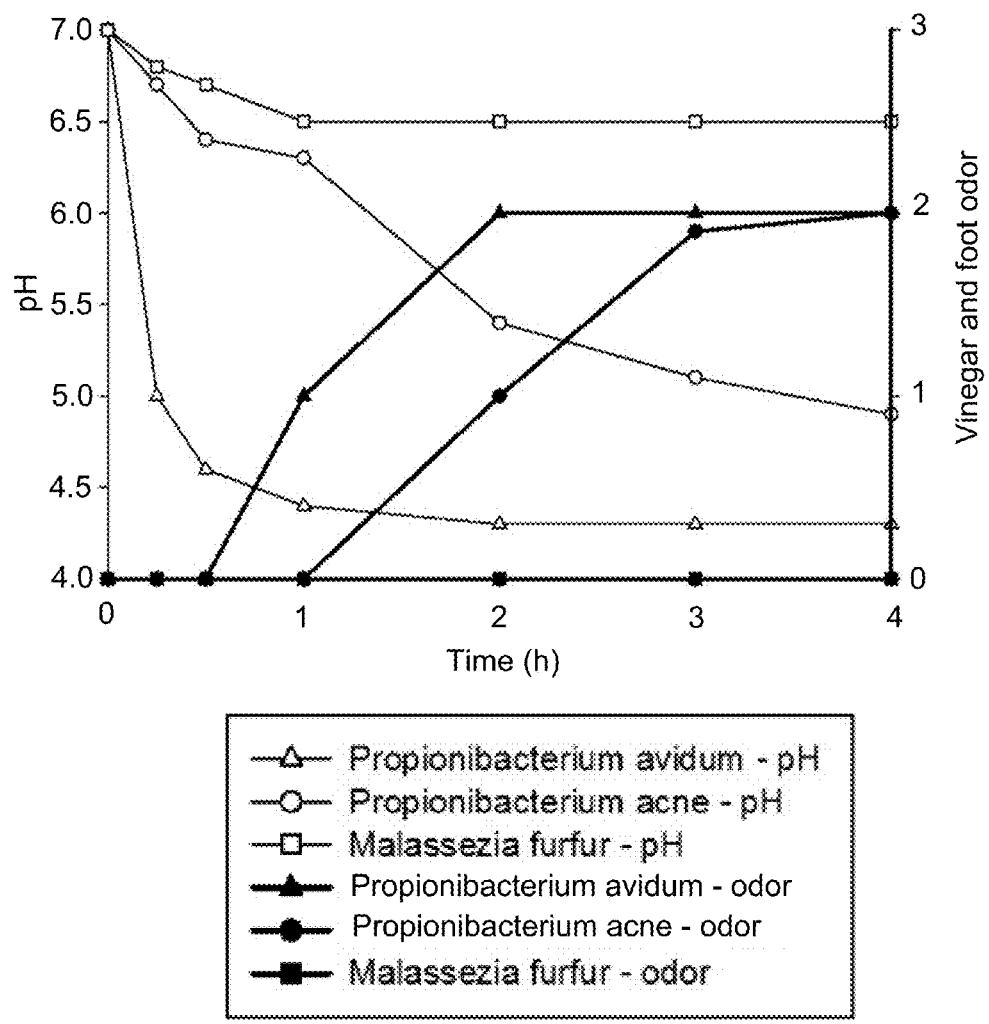
FIG. 4 is a graph showing the pH and odor responses of *Propionibacteria* and *Malassezia furfur* to 28 mM glucose.
Figure 5:
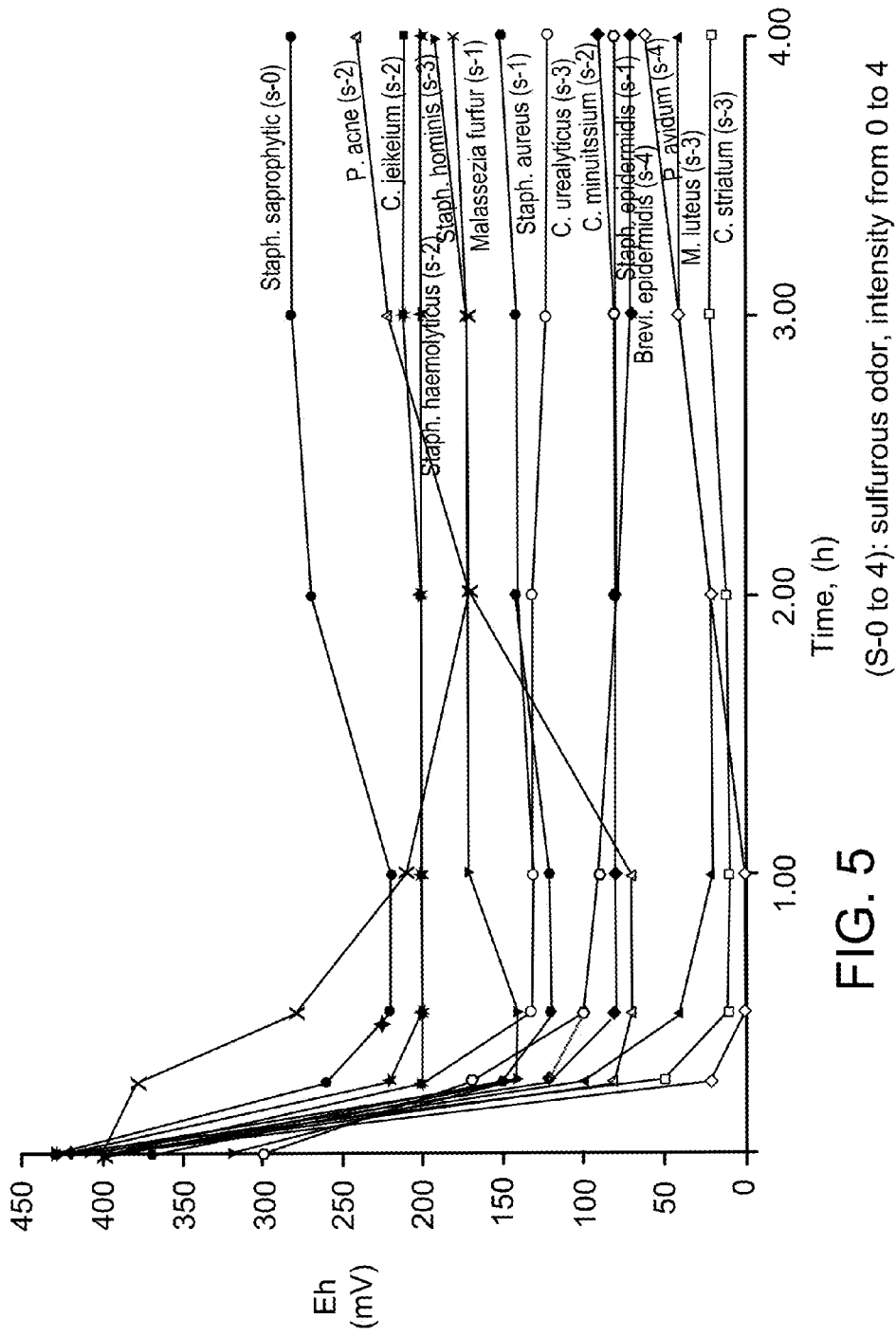
FIG. 5 is a graph showing the $E_h$ responses of axillary microflora bacteria to 6.0 mM cysteine.
Figure 6:
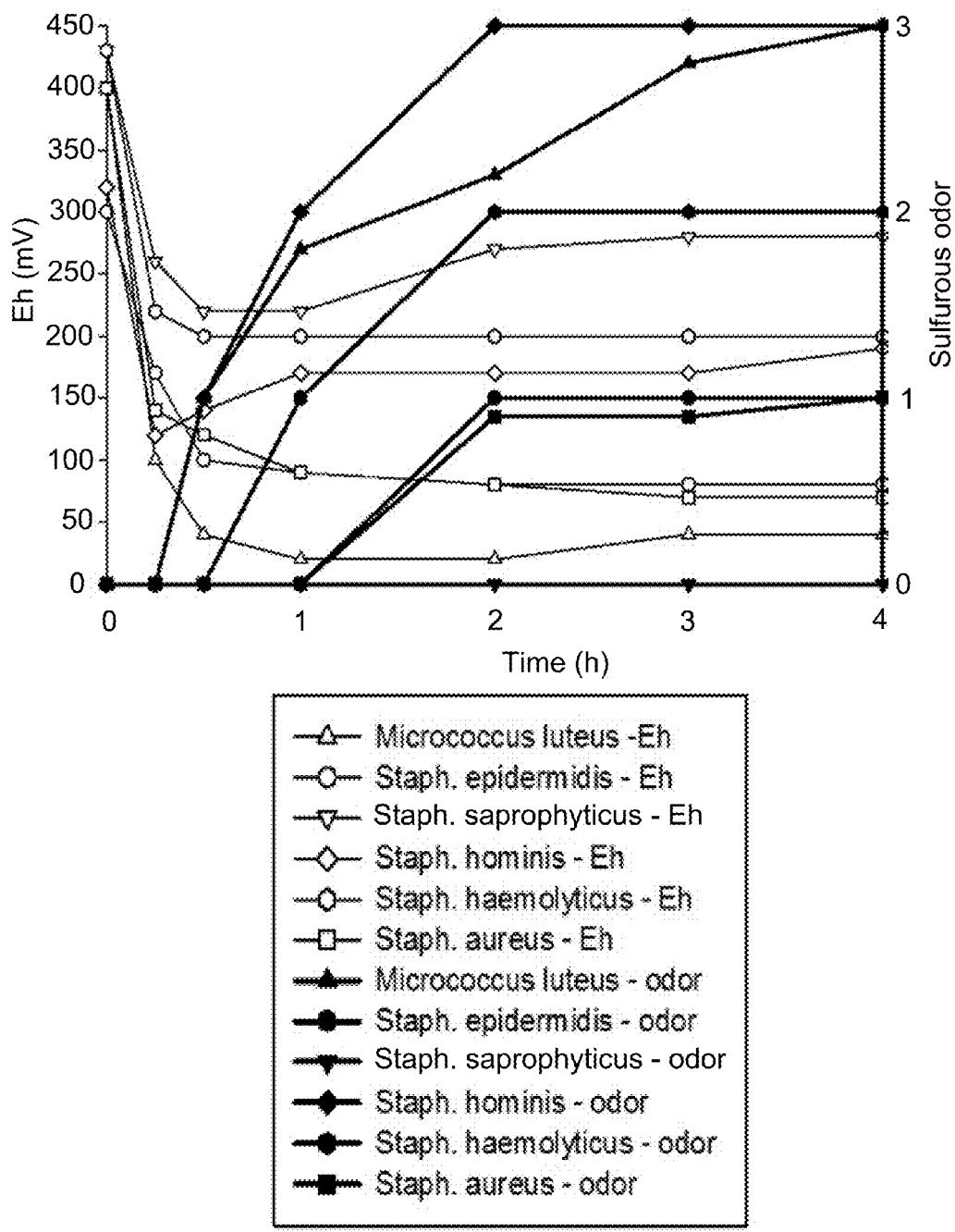
FIG. 6 is a graph showing the $E_h$ and odor responses of *Staphylococci* and *Micrococcus luteus* to 6.0 mM cysteine.
Figure 7:
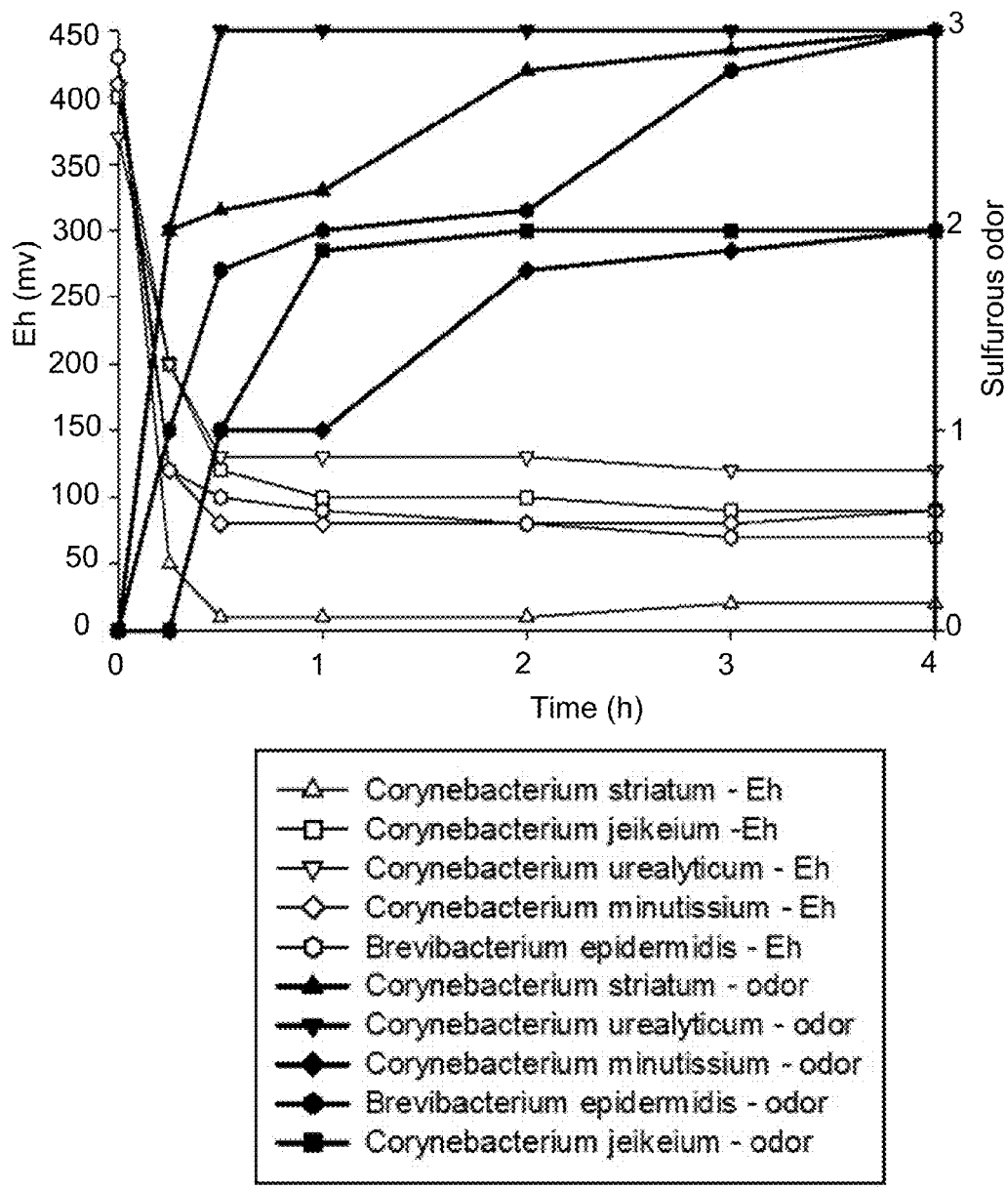
FIG. 7 is a graph showing the $E_h$ and odor responses of *Corynebacteria* and *Brevibacterium epidermidis* to 6.0 mM cysteine.
Figure 8:
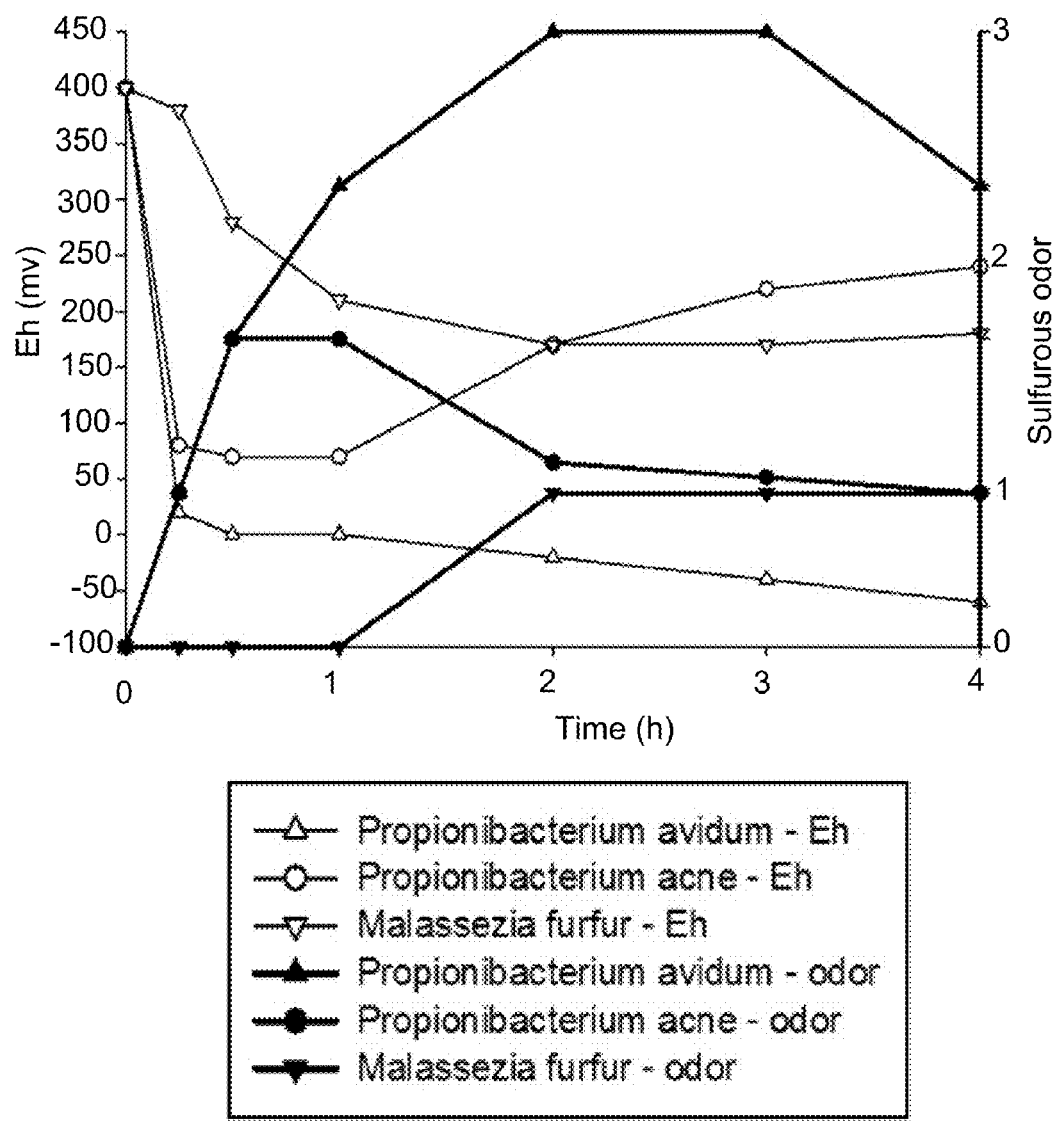
FIG. 8 is a graph showing the $E_h$ and odor responses of *Propionibacteria* and *Malassezia furfur* to 6.0 mM cysteine.

Results (i) Glycolytic Activities of Individual Pure Cultures as Indicated by Ability to Alter the pH with Each of the Various Test Substrates All of the microorganisms tested except for *Brevibacterium epidermidis* and the fungus, *Malassezia furfur* utilized one or more of the test carbohydrates, as indicated by the ability to decrease the pH during each of the various 4 hour incubations. The pH responses with the various bacteria tested varied between neutrality and a pH of 4.1 (FIG. 1). All but *M. luteus, Staph. saprophyticus, Staph. hominis, C. striatum*, and *C. minutissium* released a one type, vinegar-like acid odor and/or typical foot odor, which varied in intensity from a score of 1 to a score of 3 on a 0 to 4 scale. The greater the pH decrease, the greater the odor intensity observed (see FIGS. 2, 3 and 4).

All of the bacteria tested, except for *Brevibacterium epidermidis* utilized glucose during their respective 4 hours of incubation and produced acidic pH responses that varied from pH 7.0 all the way down to a pH of 4.2. More than half of the tested bacteria except for *Brevibacterium epidermidis, M. luteus, Staph. saprophyticus, Staph. hominis, C. striatum*, and *C. minutissium* released a vinegar-like and/or foot-web odor, as the pH became more acidic. Scores were mainly at odor severity levels of 1 or 2.

All of the bacteria tested, except for *Brevibacterium epidermidis, C. jeikeium* and *P. acne* utilized sucrose during their respective 4 hour incubations. Corresponding acidic pH responses ran from pH 7.0 down to pH 4.2. More than half of the bacteria explored, except for *M. luteus, Staph. saprophyticus, C. striatum, C. minutissium*, and *P. avidum*, produced the vinegar and/or foot odor aroma with scores at levels of 1 and 2, when the pH became increasingly acidic.

Only a few bacteria were able to utilize the other carbohydrates tested and in doing so, released, as indicated above, a mild vinegar and/or foot odor aroma. Collectively, bacterial degradation of the wide range of carbohydrate substrates tested gave only slight to moderate malodor.

Figure 9:
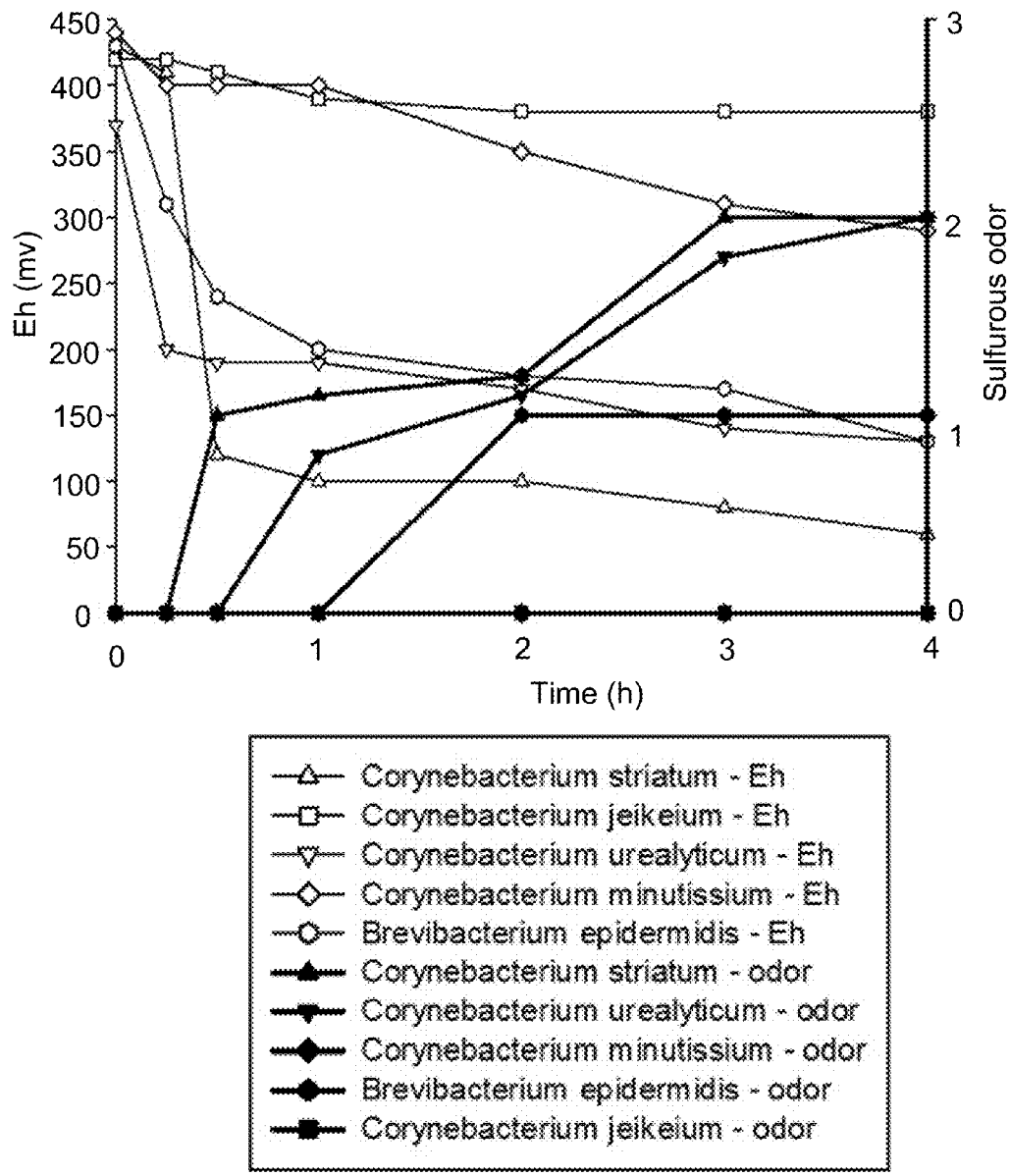
FIG. 9 is a graph showing the $E_h$ and odor responses of *Corynebacteria* and *Brevibacterium epidermidis* to 6.0 mM cystine.
Figure 10:
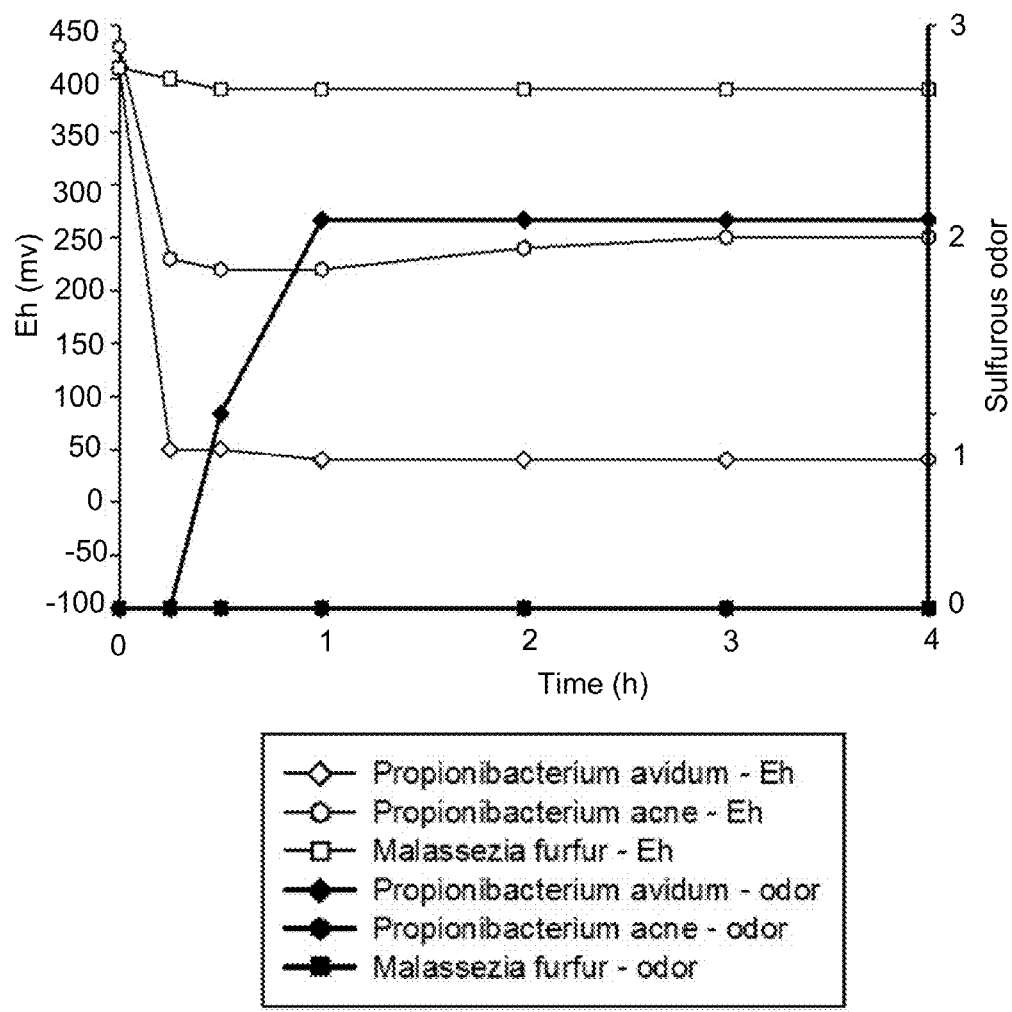
FIG. 10 is a graph showing the $E_h$ and odor responses of *Propionibacteria* and *Malassezia furfur* to 6.0 mM cystine.

(ii) Catabolism of Amino Acids by Individual Pure Cultures and Relation of Each to the $E_h$ and to the Generation of Malodor Particularly interesting was the observation that the $E_h$ decreased during the catabolism of cysteine with all of the bacteria tested (see FIGS. 5, 6, 7, 8) albeit to varying degrees. The $E_h$ also decreased during catabolism of cystine and cysteine by *C. striatum, C. urealyticus, Brevibacterium epidermidis*, and *P. avidum* (FIGS. 9, 10). The two largest decreases occurred with *C. striatum* and *P. avidum*. All of the bacteria that showed an $E_h$ decrease, released a sulfurous odor. The strongest sulfurous odor occurred with *C. striatum, C. jeikeium, C. urealyticum, Brevibacterium epidermidis, Staph. hominis, M. luteus*, and *P. avidum*. Also, all of the bacteria that catabolized cystine and cysteine released a similar sulfurous odor (FIGS. 9, 10).

Figure 11:
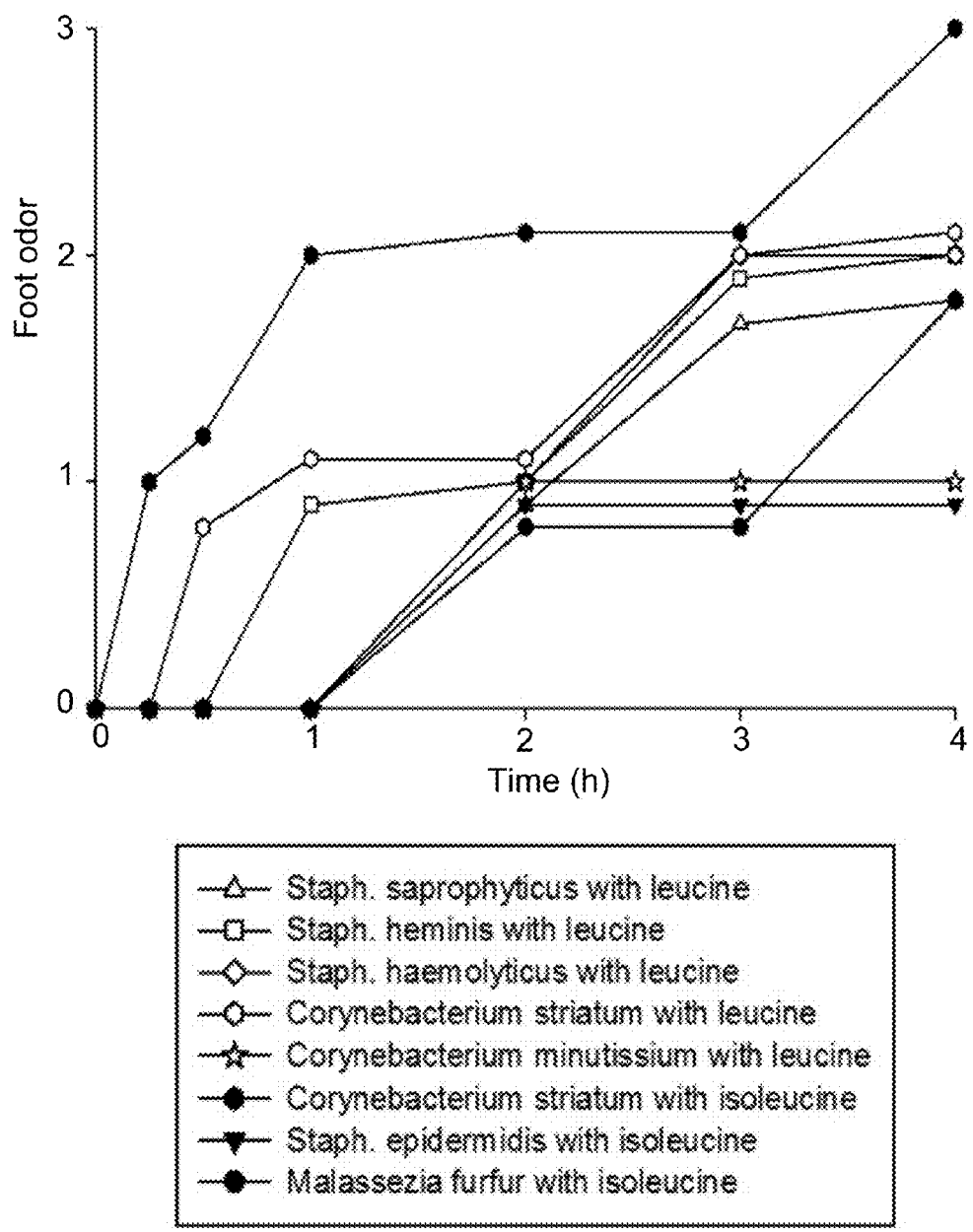
FIG. 11 is a graph showing the odor responses of axillary microflora bacteria to 6.0 mM leucine or 6.0 mM isoleucine.

*Staph. saprophyticus, Staph. hominis, Staph. haemolyticus*, and *C. minutissium* readily catabolized leucine. These produced a foot-web odor at a score level of 2. Iso-leucine was catabolized by *Staph. epidermidis* and the yeast, *M. furfur*; the latter stimulated release of the foot odor smell at levels of 1 or 2. *C. striatum* was able to catabolize both leucine and iso-leucine and produce relatively strong foot odor at intensity levels of 2 and 3 (FIG. 11).

Figure 12:
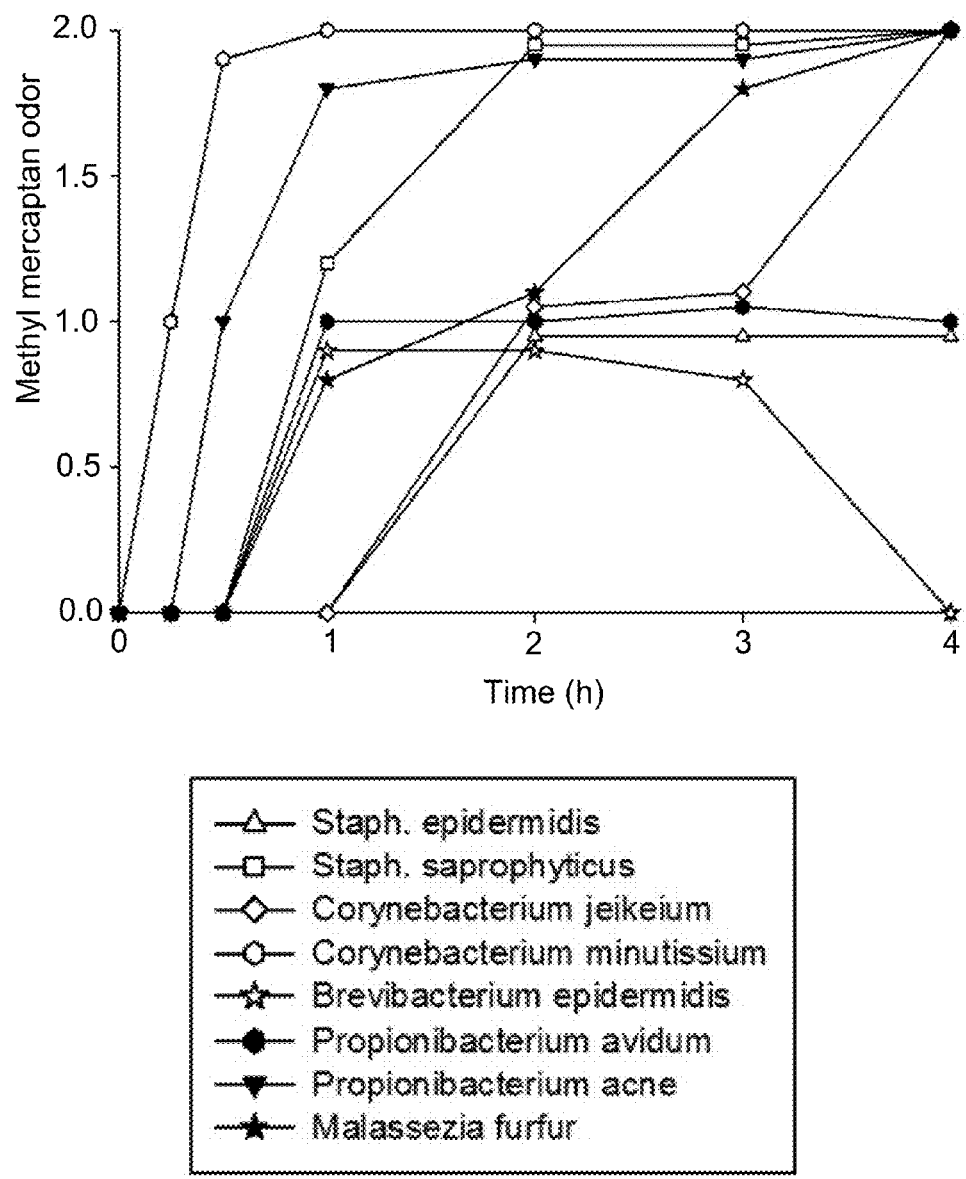
FIG. 12 is a graph showing the odor responses of axillary microflora bacteria to 6.0 mM methionine.

Each of the bacteria, *Staph. epidermidis, Staph. saprophyticus, C. jeikeium, C. minutissium, Brevibacterium epidermidis, P. avidum, P. acne* and *M. furfur* were able to utilize methionine and produce a methyl mercaptan-like odor at a mild to moderate level (FIG. 12).

Figure 13:
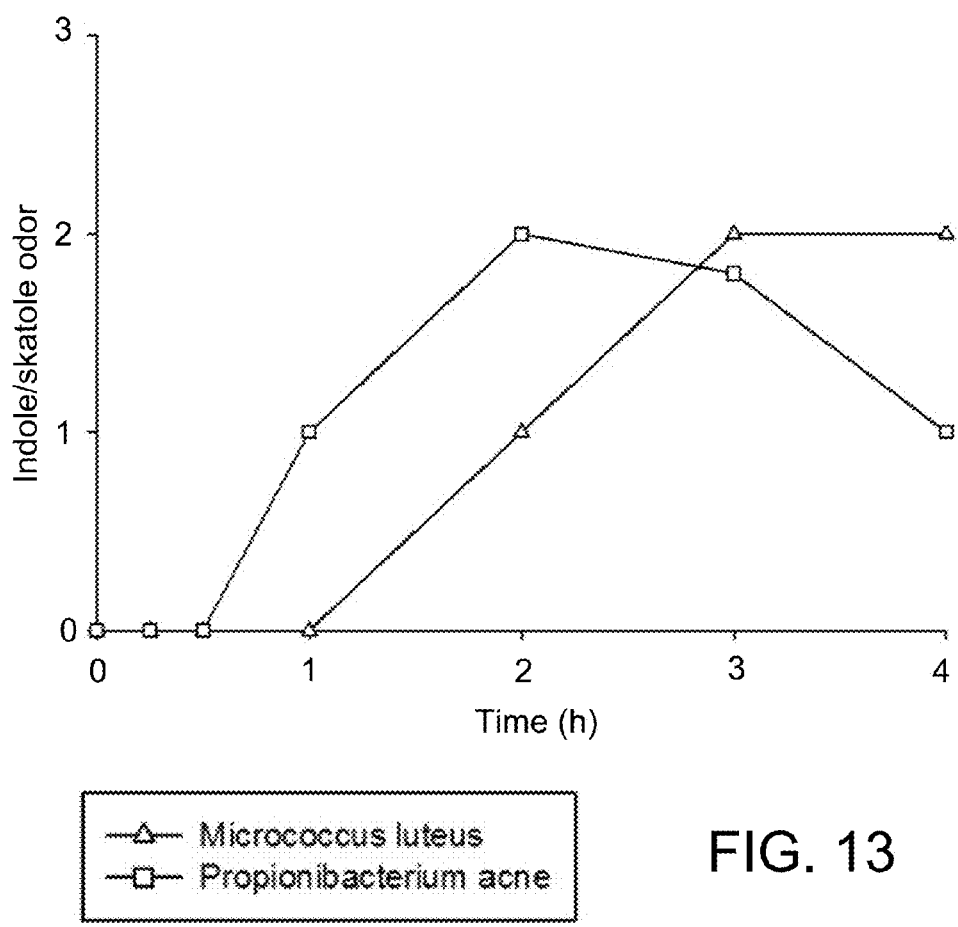
FIG. 13 is a graph showing the odor responses of *Micrococcus luteus* and *Propionibacterium acne* to 6.0 mM tryptophan.
Figure 14:
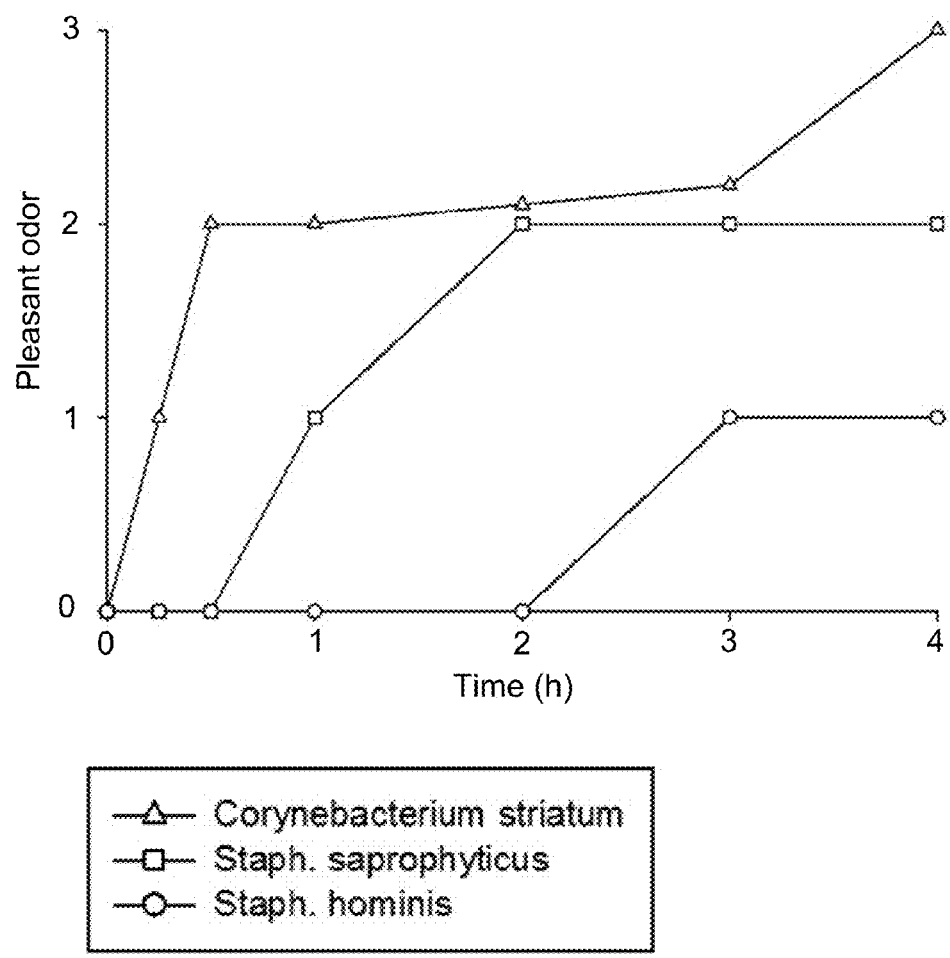
FIG. 14 is a graph showing the pleasant odor responses of *Corynebacterium striatum*, *Staphylococcus saprophyticus*, and *Staphylococcus hominis* to 6.0 mM phenylalanine.

Tryptophan was catabolized by *M. luteus* and *P. acne* and resulted in release of an indole/skatole odor at an odor level of 2 (FIG. 13). Surprisingly, a pleasant odor was produced when phenylalanine was catabolized by *C. striatum, Staph. saprophyticus*, or *Staph. hominis*. *C. striatum* was able to release this pleasant odor at odor levels of 2 to 3 (FIG. 14).

Except for cysteine and cystine, no obvious $E_h$ or pH changes were detected by the various microorganisms tested, except for a pH increase with arginine.

(iii) pH Changes and Odor Generation During Arginolysis Observed with *Staph. epidermidis, Staph. Haemolyticus* and *P. avidum*

Figure 15:
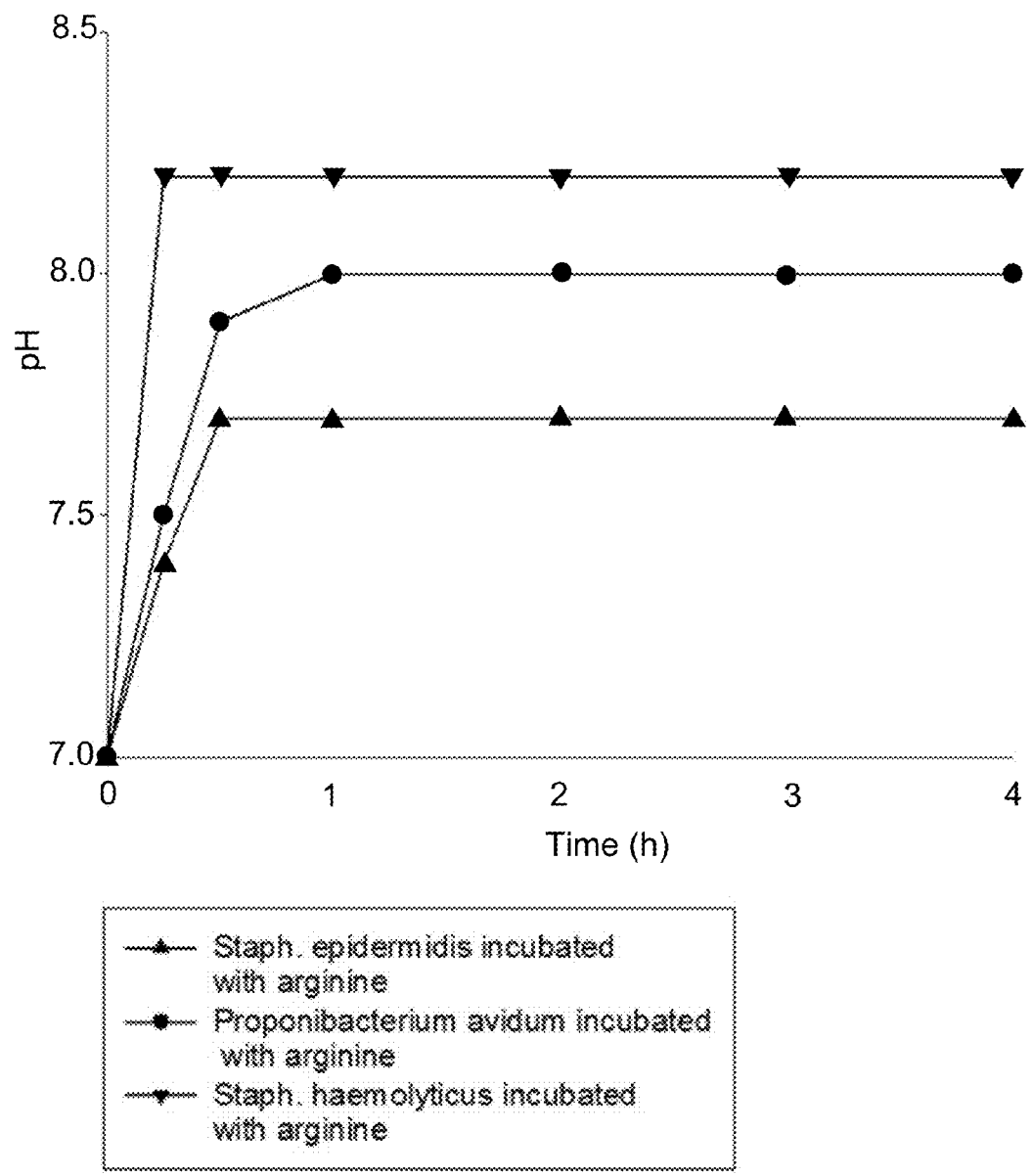
FIG. 15 is a graph showing the pH responses of *Staphylococcus epidermidis*, *Propionibacterium avidum* and *Staphylococcus haemolyticus* to 6 mM arginine.

When these three microorganisms were each incubated with 6.0 mM arginine, the pH of *Staph. epidermidis* rose from 7.0 to 7.4 within the first 15 min and continued to rise slowly thereafter to a pH of 7.7 by the end of the 4 hours of incubation. The pH of *P. avidum*, when incubated with arginine, rose to a higher level than that with *Staph. epidermidis* by about 0.3 pH units. The pH of *Staph. haemolyticus* during arginolysis reached a value of 8.2, which was the highest pH reached of these three bacteria tested (FIG. 15). No odor of significance was detected with any of these microorganisms.

(iv) Hydrogen Peroxide Production

When the various bacteria were incubated with the spectrum of carbohydrate and amino acid substrates tested, no hydrogen peroxide was produced with any of them.

Example II

Effects of (i) Zinc Salts and (ii) Arginine Free Base Plus Arginine Bicarbonate on pH, $E_h$ and Odor Formation with the Microorganisms Able to Produce Changes when Incubated with Various Amino Acid Substrates The experiments in this segment focused mainly on *C. striatum* and *Staph. epidermidis*, because these two bacterial species proved to be the most prominent components of the skin axillary microflora involved (Taylor et al., 2003, Nobel, 1992, Leyden et al., 1981, Shehaden et al., 1963) in the production of axillary malodor. The most prominent malodor generating substrates from the experiments in Example I above were determined to be cysteine, isoleucine and leucine (CIL). Accordingly, they were examined together in this Example as a mixture of substrates with *C. striatum* and *Staph. epidermidis* as a mixture of bacteria. With such a combination, these experiments essentially examined the bulk of the malodor generating capability of the axillary microflora with the bulk of the malodor generating substrates.

Materials and Methods

Preparation of a *C. striatum* and *Staph. epidermidis* Pure Culture Bacterial Mixture and Incubation of the Stock Solutions Pure cultures of *C. striatum* and *Staph. epidermidis* were prepared by the same methods as described in Example I above. A mixture of these two bacteria was then prepared, wherein the total bacterial composition was 50% by volume, with *C. striatum* and *Staph. epidermidis* each at 25% (v/v).

Twenty ml of two stock solutions were prepared, where one was comprised of 54 mM and the other with 72 mM of each of cysteine, isoleucine and leucine. Similarly, 20 ml stock solutions of 144 mM of phenylalanine was also prepared.

Zinc Salts for Use in Odor Inhibitions

Stock solutions of the following zinc salts were prepared. The zinc salts selected were chosen to do two things. One was to provide zinc as an inhibitor of cysteine degradation (Pader, 1988; Kleinberg and Codipilly, 2008) and inhibition of odor generation therefrom. The other was to select accompanying anions that provided means of pH adjustment without needing to add buffers that might introduce additional and unnecessary ions.

Accordingly, zinc salts were dissolved in deionized water and provided in various salt forms as follows:

(a) Zinc citrate: 10 ml of 36 mM zinc citrate partially dissolved (i.e., dissolved to the extent possible) in de-ionized water, which gave a pH of 4.2.

(b) Zinc chloride: 10 ml of 36 mM zinc chloride dissolved in de-ionized water, which gave a respective pH value of 6.7.

(c) Zinc acetate: 2 different concentrations of zinc acetate were prepared.
   10 ml of 36 mM dissolved in de-ionized water.
   10 ml of 72 mM dissolved in de-ionized water.
   Both gave a pH of 6.8.
(d) Zinc lactate dehydrate: 10 ml of 36 mM zinc lactate dehydrate dissolved in de-ionized water, which gave pH values between 6.3 and 6.8. Zinc lactate dehydrate could not be dissolved completely.
(e) Zinc carbonate: basic zinc carbonate ($ZnCO_3 \cdot 3\ Zn(OH)_2$); 10 ml of 36 mM and 10 ml of 72 mM of this salt was used. It had a pH of 8.2. Its solubility in water was limited. $ZnCO_3$ by itself has a pH of 7.3-7.5.
(f) Zinc arginate: 10 ml of 36 mM. It gave a pH of 10.0. It completely dissolved in water between pH 5.0 and 6.0 and only partly, if the pH was at 5.0.

Experimental Procedures

The experimental procedures for the incubations in this section were basically the same as in Example I. The only differences were in the concentrations of the different stock solutions chosen, when different combinations of media were prepared (see Tables 2.1, 2.2, and 2.3).

The pH of the medium with each of the different zinc salts needed some adjustment, which was done with 1 M HCl or 1 M NaOH depending upon the pH of the stock solutions of each zinc salt employed. Accordingly, the test medium was pH 4.0 with zinc citrate, pH 5.0 with zinc chloride, pH 6.0 with zinc acetate, pH 7.0 with zinc lactate, and pH 8.0 with zinc carbonate.

TABLE 2.1

Bacterial suspension (8.3% v/v) incubated with (i) 12 mM zinc salt* and (ii) 6 mM cysteine, 6 mM leucine and 6 mM isoleucine

| | | Samples | | | |
|---|---|---|---|---|---|
| | | Experimental samples | | Negative control | |
| Composition | | vol. (ml) | Final conc. | vol. (ml) | Final conc. |
| a.a. | Cys 54 mM | 0.1 | 6 mM | 0.1 | 6 mM |
| | Leu 54 mM | 0.1 | 6 mM | 0.1 | 6 mM |
| | Ileu 54 mM | 0.1 | 6 mM | 0.1 | 6 mM |
| Zinc salt* 36 mM | | 0.3 | 12 mM | — | — |
| Microorganism suspension 25% (v/v) | | 0.3 | 8.3% | 0.3 | 8.3% |
| D-water | | — | — | 0.3 | — |
| Total volume (ml) | | 0.9 | | 0.9 | |

*Zinc salts included zinc citrate, zinc chloride, zinc acetate, zinc lactate or zinc carbonate

TABLE 2.2

Bacterial suspension (8.3% v/v) incubated with (i) 12 mM zinc arginate and (ii) 6 mM cysteine, 6 mM leucine, 6 mM isoleucine and 12 mM phenylalanine

| | | Samples | | | |
|---|---|---|---|---|---|
| | | Experimental samples | | Negative control | |
| Composition | | vol. (ml) | Final conc. | vol. (ml) | Final conc. |
| a.a. | Cys 72 mM | 0.075 | 6 mM | 0.075 | 6 mM |
| | Leu 72 mM | 0.075 | 6 mM | 0.075 | 6 mM |
| | Ileu 72 mM | 0.075 | 6 mM | 0.075 | 6 mM |
| | Phe 144 mM | 0.075 | 12 mM | 0.075 | 12 mM |
| Zinc arginate salt 36 mM | | 0.3 | 12 mM | — | — |
| Microorganism suspension 25% (v/v) | | 0.3 | 8.3% | 0.3 | 8.3% |
| D-water | | — | — | 0.3 | — |
| Total volume (ml) | | 0.9 | | 0.9 | |

TABLE 2.3

Bacterial suspension (8.3% v/v) incubated with (i) 12 mM zinc carbonate and 12 mM arginine bicarbonate or (ii) 12 mM arginine, 6 mM cysteine, 6 mM leucine, 6 mM isoleucine and (iii) 12 mM phenylalanine

| | | Samples | | | |
|---|---|---|---|---|---|
| | | Experimental samples | | Negative control | |
| Composition | | vol. (ml) | Final conc. | vol. (ml) | Final conc. |
| a.a. | Cys 72 mM | 0.075 | 6 mM | 0.075 | 6 mM |
| | Leu 72 mM | 0.075 | 6 mM | 0.075 | 6 mM |
| | Ileu 72 mM | 0.075 | 6 mM | 0.075 | 6 mM |
| | Phe 144 mM | 0.075 | 12 mM | 0.075 | 6 mM |
| Zinc carbonate 72 mM | | 0.15 | 12 mM | — | — |
| Arginine bicarbonate 72 mM or Arginine 72 mM | | 0.15 | 12 mM | | |
| Microorganism suspension 25% (v/v) | | 0.3 | 8.3% | 0.3 | 8.3% |
| D-water | | — | — | 0.3 | — |
| Total volume (ml) | | 0.9 | | 0.9 | |

Figure 16A:
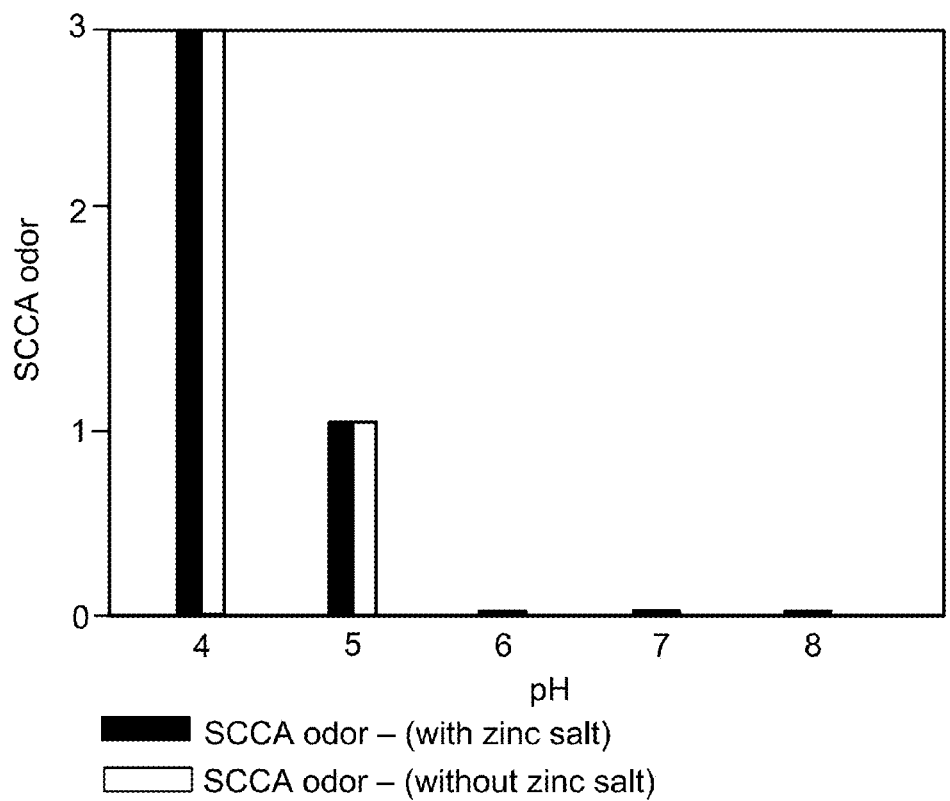
FIG. 16A and FIG. 16B are graphs showing the short chain carboxylic acid (SCCA) (FIG. 16A) and sulfurous (FIG. 16B) odor in relation to pH when 8.3% (v/v) *Corynebacterium striatum* was incubated with 12.0 mM zinc salt buffer and 6.0 mM of cysteine, isoleucine and leucine (CIL) at 37° C. for 4 hours.
Figure 16B:
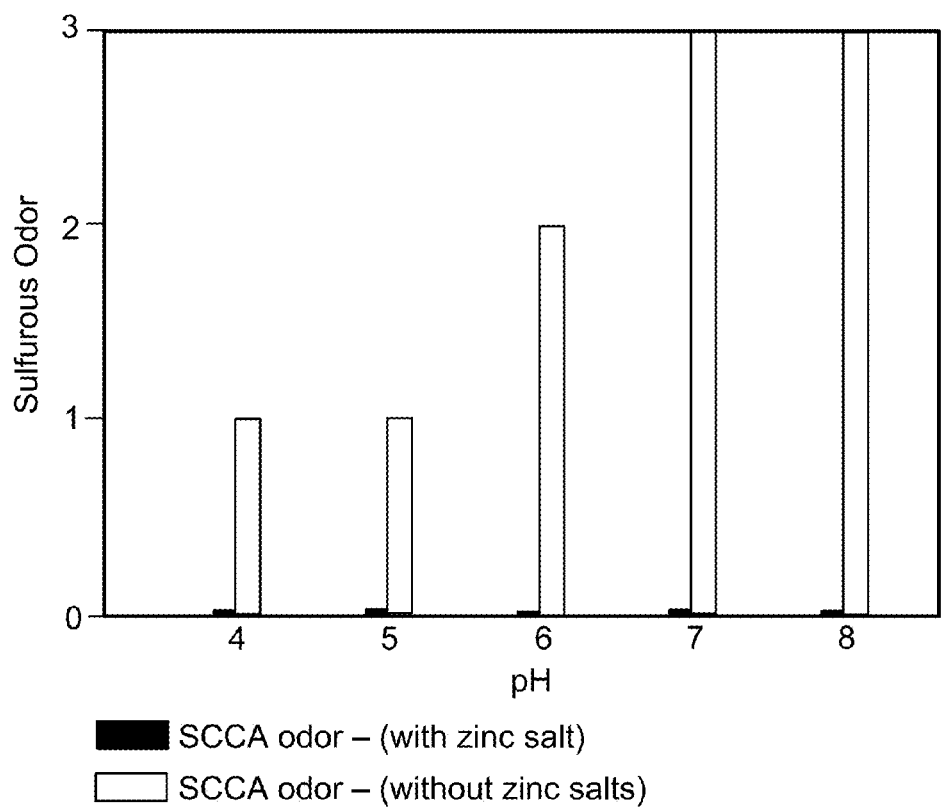

Results (i) The Effects of a Series of Zinc Salts on Malodor Generation when Each was Incubated for 4 Hours with *C. striatum* and *Staph. Haemolyticus* in Incubation Mixtures Containing Cysteine, Isoleucine and Leucine When either *C. striatum* or *Staph. haemolyticus* were incubated with the cysteine, isoleucine and leucine amino acid combination in the presence of zinc salts, generation of sulfurous odor was blocked almost completely at pH values between 4.0 and 8.0 for the full incubation period of 4 hours. At the same time, the $E_h$ correspondingly failed to decrease dramatically (FIG. 16 (A and B)).

Foot-web odor was detected when *C. striatum* or *Staph. haemolyticus* was incubated in the above media between pH 4.0 and 6.0, even with zinc salts present. The lower the pH in this range, the more intense the foot odor observed, viz. it was strongest at pH 4.0 and 4.5 and gradually weaker, as the pH increased to pH 6.0. Above this level, foot odor generation completely disappeared (see FIG. 16 (A and B)).

Figure 17:
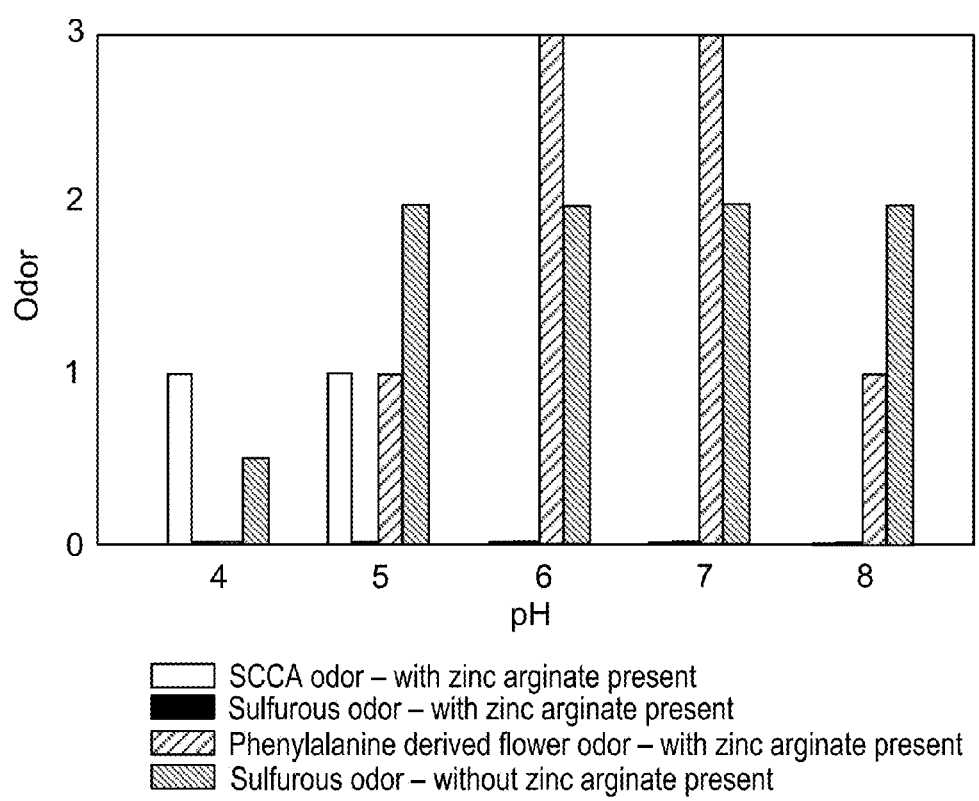
FIG. 17 is a graph showing the SCCA, sulfurous and pleasant odor in relation to pH when an 8.3% (v/v) 1:1 mixture of *Corynebacterium striatum* and *Staphylococcus epidermidis* was incubated with 12.0 mM zinc arginate, 6.0 mM CIL and 12.0 mM phenylalanine at 37° C. for 4 hours.

(ii) The Effect of Zinc Arginate on Odor, when *C. striatum*, *Staph. epidermidis* and a Mixture of the Two at a Ratio of 1 to 1 were Incubated with Cysteine, Isoleucine, Leucine and Phenylalanine Sulfurous odor was blocked completely in comparison to control groups, when *C. striatum*, *Staph. epidermidis* or a mixture of the two were each incubated for 4 hours with the cysteine, isoleucine, leucine and phenylalanine combination, both in the presence and in the absence of zinc arginate at pH 4.0 to pH 8.0. Correspondingly, $E_h$ decreased significantly (FIG. 17).

A mild foot odor smell was detected when *C. striatum*, *Staph. epidermidis* or a 1:1 combination thereof were each incubated in the above media with zinc arginate for 4 hours at pH 4.0 or 5.0. Odor generation disappeared, when the pH was higher, i.e. at 6.0 or above (see FIG. 17).

Once more, a favorable odor was evident when *C. striatum* or the mixture of *C. striatum* and *Staph. epidermidis* were incubated in the above media with zinc arginate for 4 hours at pH 5.0 to 8.0. The favorable odor increased as the pH was elevated (FIG. 17). The pleasant flower odor was not detected when *Staph. epidermidis* was incubated for 4 hours alone in the above incubation mixtures with zinc arginate present. Evidently, *Staph. epidermidis* is not able to decompose phenylalanine and produce the pleasant odor that normally occurs with phenylalanine decomposition (e.g., when *C. striatum* is present).

(iii) Demonstration that Arginine and Arginine Bicarbonate Favored Odor Release when *C. striatum*, *Staph. epidermidis* and their Mixture in the Ratio of 1 to 1 were Incubated for 4 Hours in a Medium Containing Zinc Acetate, Cysteine, Isoleucine, Leucine with or without Phenylalanine No sulfurous odor nor corresponding decrease in the $E_h$ was observed when *C. striatum, Staph. epidermidis* or a 1:1 mixture thereof were incubated in the presence of either (i) zinc acetate, (ii) cysteine, isoleucine, leucine and (iii) either arginine or arginine bicarbonate between pH 4.0 and 8.0. Incubations were carried out for 4 hours and with no phenylalanine present.

A moderate to strong vinegar odor was observed, when *C. striatum, Staph. epidermidis* and a mixture thereof were incubated in the above media for 4 hours at pH 4.0 to 5.0. Also, as before, no odor was generated when the pH was increased to 6.0. A very mild, not unpleasant amine odor could be detected when the pH was raised to a pH of 7.5 or 8.0.

A pleasant odor appeared when phenylalanine was introduced into the above media and incubated with the mixture of *C. striatum* and *Staph. epidermidis* for 4 hour at pH 6.5 and 7.0.

Figure 18:
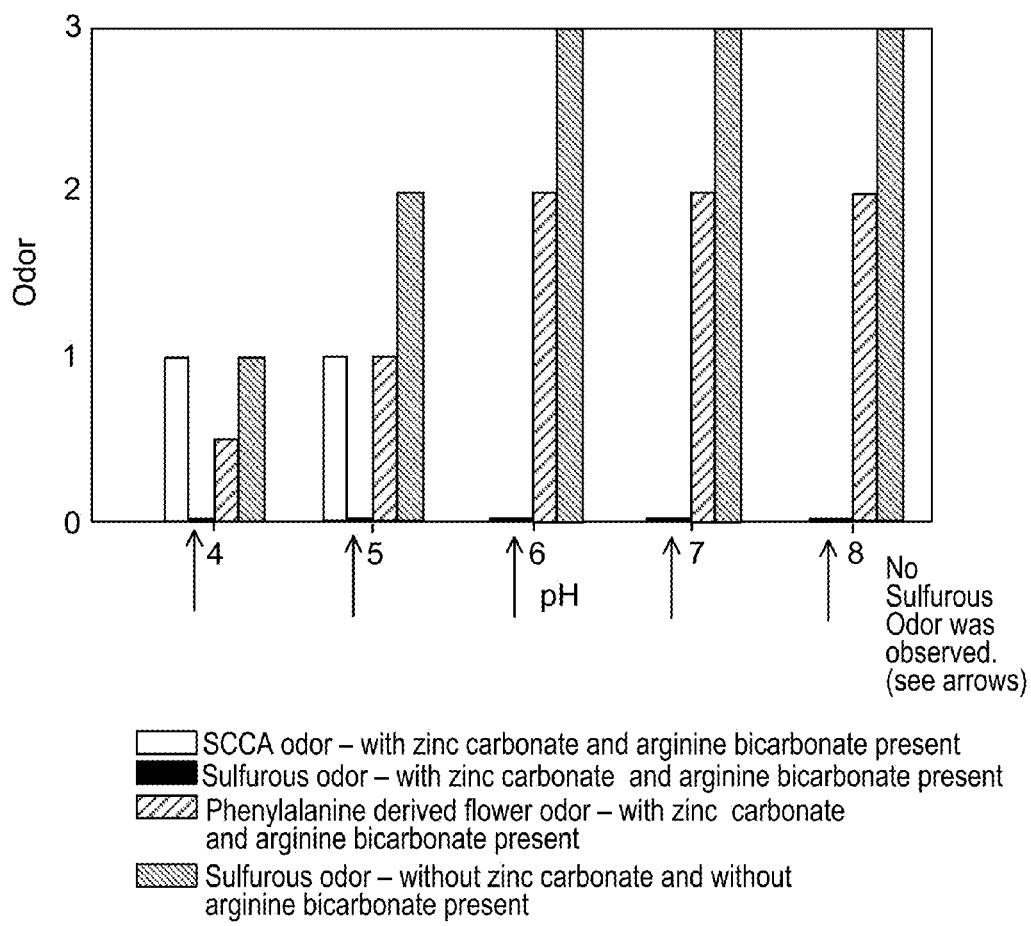
FIG. 18 is a graph showing the SCCA, sulfurous and pleasant odor in relation to pH when an 8.3% (v/v) 1:1 mixture of *Corynebacterium striatum* and *Staphylococcus epidermidis* was incubated with 12.0 mM zinc carbonate, 12.0 mM arginine bicarbonate, 6.0 mM CIL and 12.0 mM phenylalanine at 37° C. for 4 hours.

(iv) Effect of Arginine Bicarbonate on Odor when the Mixture of *C. striatum* and *Staph. epidermidis* in the Ratio of 1 to 1 was Incubated in the Presence of Zinc Carbonate, Cysteine, Isoleucine, Leucine and Phenylalanine at pH 4.0 to 8.0 for 4 Hours When the mixture of *C. striatum* and *Staph. epidermidis* in the ratio of 1 to 1 was incubated in a medium containing zinc carbonate, cysteine, isoleucine, leucine and phenylalanine at pH 4.0 to 8.0 for 4 hours, by and large, no sulfurous odor was observed (FIG. 18).

Also, a pleasant odor developed from phenylalanine when the above media were incubated with the mixture of *C. striatum* and *Staph. epidermidis* for 4 hours between pH 5.0 and 8.0 (FIG. 18). In contrast, a mild odor of foot and pleasant flower odor occurred when a mixture of these two bacteria were incubated in the above media at a pH between 4.0 and 5.0 (FIG. 18).

Figure 19:
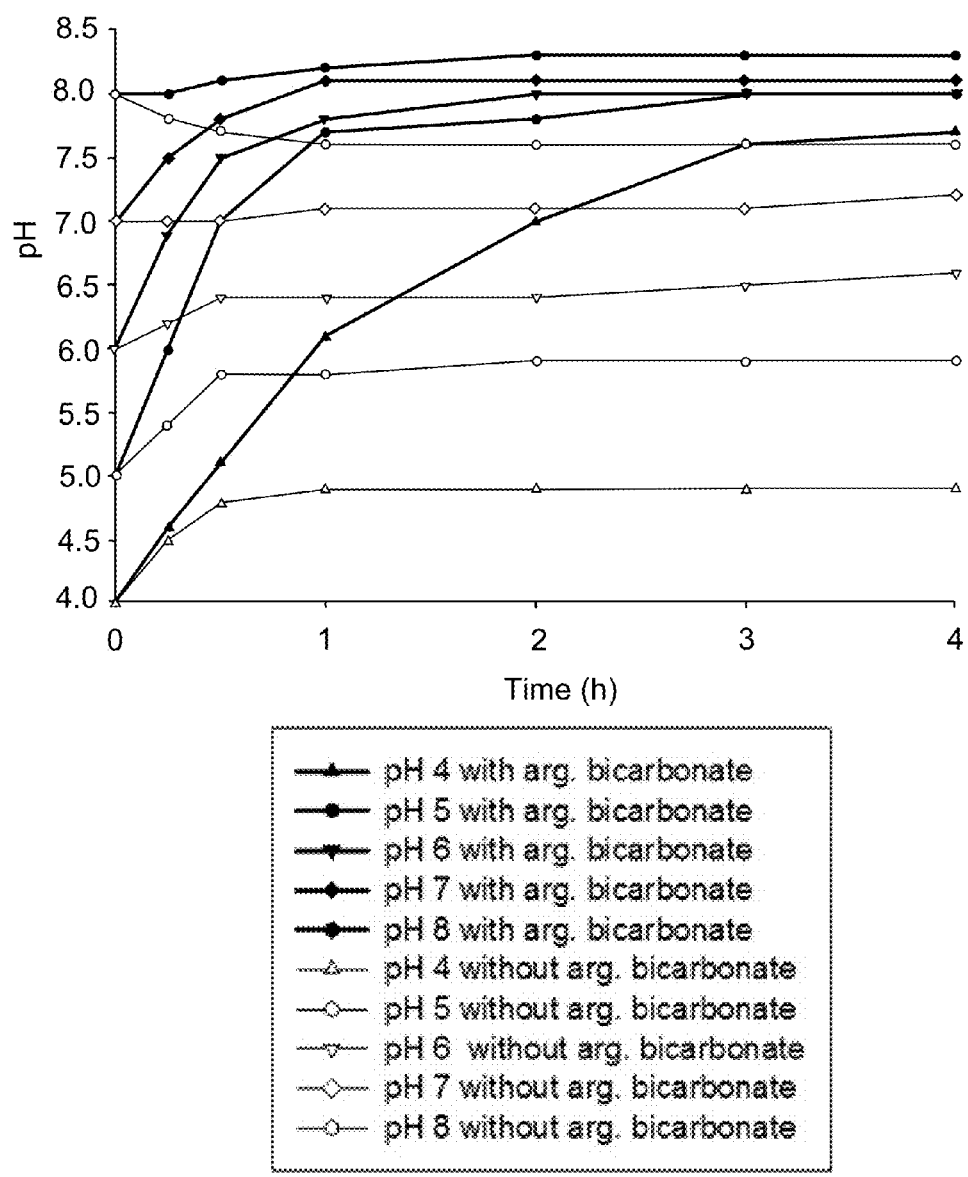
FIG. 19 is a graph showing the effect of 12.0 mM arginine bicarbonate on the pH of an 8.3% (v/v) 1:1 mixture of *Corynebacterium striatum* and *Staphylococcus epidermidis* incubated with 6.0 mM CIL and 12.0 mM phenylalanine at 37° C. for 4 hours.

The results showed that arginine bicarbonate could serve as a strong alkaline buffer, which enabled the pH to be maintained at about 8.0, in the above amino acid media with the mixture of these two bacteria for 4 hours of incubation at 37° C. in comparison with the same media without arginine (see FIG. 19). Also, when zinc carbonate was introduced into the above samples, arginine bicarbonate still tended to raise the pH, especially in media, where the pH was originally set between 6.0 and 8.0. For example, the medium at pH 6.0 rose to 6.8; one at pH 7.0 rose to 7.8, and one at 8.0 remained at 8.0. A pH above 8.0 could be obtained by adding some zinc hydroxide.

Example III

Effect of pH on the Production of Foot Odor

Two types of experiments were performed here. One type was where the incubation, as in Example II above was for 4 hours at 37° C. with the pH between 4.0 and 8.0 and odor was checked during the entire period of incubation. The second type of experiment involved preparation of artificial foot odorants (as described below) and (i) assessing foot odor formation at various pH levels arising from these samples during their incubation at 37° C. and (ii) titrating such samples with deodorant formulation (zinc carbonate plus arginine bicarbonate (ABZC)) to assess its effects on the artificial foot odor.

Materials and Methods

Pure Cultures of Microorganisms Tested

For the experiments in this part of this investigation, pure cultures of *C. striatum, Staph. haemolyticus* and *P. avidum* were prepared as described above.

Preparation of Artificial Foot Odorants

Stock solutions were prepared that simulated foot odor (i.e., artificial foot odorants). This was done by mixing stock solutions of short chain carboxylic (fatty) acids (SCCAs) that have been identified as being components of foot odor. Types of SCCAs potentially involved included acetic, butyric, isobutyric, propionic, valeric and isovaleric acids. These are basically oily liquids and produce volatile unpleasant, often rancid odors, in their acidic non-ionized forms. SCCAs do not volatilize when they are in their ionized base forms, which are favored by a higher pH. Mixing SCCAs at different concentrations has enabled development of odor compositions like those of foot odor.

(1) Preparation of a Stock Solution Containing Artificial Foot Odorant.

The fatty acids assembled for the purpose of constructing an artificial foot odorant included acetic acid (purity 100%, obtained from Fisher Scientific Fair Lawn, N.J. USA) and butyric, isobutyric, propionic, valeric and isovaleric acids (purity 99%, obtained from Sigma-Aldaichand St. Louis, Mo. USA). The following table was then constructed to dilute each fatty acid in preparation for formulation of the artificial foot odorant.

TABLE 3.1

| # Sample | 1 | 2 | 3 | 4 | 5 | 6 | 7 | 8 | 9 | 10 | 11 |
|---|---|---|---|---|---|---|---|---|---|---|---|
| Dilution | 1:1 | 1:3 | 1:7 | 1:15 | 1:31 | 1:63 | 1:127 | 1:225 | 1:525 | 1:1019 | 1:2024 |
| Conc. of original (%) | 50 | 25 | 12.5 | 6.25 | 3.124 | 1.56 | 0.78 | 0.39 | 0.19 | 0.098 | 0.049 |
| Fatty acid (µl) | 500 | 250 | 125 | 62.5 | 31.25 | 15.6 | 7.8 | 3.9 | 1.9 | 0.98 | 0.49 |

TABLE 3.1-continued

| # Sample | 1 | 2 | 3 | 4 | 5 | 6 | 7 | 8 | 9 | 10 | 11 |
|---|---|---|---|---|---|---|---|---|---|---|---|
| D-water (μl) | 500 | 750 | 875 | 937.5 | 968.5 | 984.4 | 992.2 | 996.1 | 998.1 | 999.02 | 999.51 |

This dilution process enabled selection of the dilution of each SCCA that would give an odor level of equal intensity, when mixed in equal volume. The results achieved were as follows.

TABLE 3.2

| | Fatty acid | | | | | |
|---|---|---|---|---|---|---|
| # of Sample | Acetic 7 | Butyric 11 | Iso-butyric 9 | Propionic 9 | Valeric 10 | Iso-valeric 9 |
| Dilution | 1:127 | 1:2024 | 1:525 | 1:525 | 1:1019 | 1:525 |

The pH of the artificial foot odorant was 3.0 and the odor level on a scale of 0 to 4 was 4, which is very strong.

Three samples of artificial foot odorant were prepared as follows and tested for pH and odor severity.

Sample I was the artificial foot odorant stock solution diluted 1 to 1 with deionized water, which gave a pH of 3.1 and an odor level of 4.

Sample II was the artificial foot odorant stock solution diluted 1 to 2 with deionized water, which gave a pH of 3.3 and an odor level of 3.

Sample III was the stock solution of artificial foot odorant diluted 1 to 3 with deionized water, which gave a pH of 3.3 and an odor level of 3.

Each sample was mixed well with a magnetic stirring bar in an Erlenmeyer flask with a glass stopper and with magnetic stirring (Corning Stirrer PC-353, Fisher Scientific 300 Industry Drive, Pittsburgh, Pa. USA).

Compositions for pH Adjustment of the Artificial Foot Odorant Samples and their Testing

TABLE 3.3

| | | Ingredients (ml) | | | | |
|---|---|---|---|---|---|---|
| Formula | pH value | Deionized water | Arginine bicarbonate | Zinc carbonate | Zinc arginate | Hydrochloric acid (1.0M) |
| 78K | 8.6 | 98.98 | 0.36 | 0.66 | — | — |
| 78L | 8.6 | 97.70 | — | — | 0.50 | 1.80 |

Experiments to Determine the Effect of pH on Odor Generation from Artificial Foot Odorants (i) Experiment 1:

Five samples of the four test bacterial cultures were prepared at a cell concentration of 25.0% (v/v). The pH of the 5 samples of *C. striatum, Staph. epidermidis, Staph. haemolyticus* and *P. avidum* were adjusted to between 4.0 and 8.0 at intervals of one pH unit using 1.0 M HCl or 1.0 M NaOH. All samples were then incubated in a water bath for 4 hours at 37° C. The pH, $E_h$ and odor were then measured at various times (0, 0.25, 0.5, 1.0, 2.0, 3.0 and 4.0 hours) throughout the incubation.

(ii) Experiment 2:

(a) Three samples (I, II and III) of the artificial foot odorants were adjusted to pH levels of 4.0, 5.0, 6.0, 7.0 and 8.0. Each test tube contained 1.0 ml of the sample and was incubated at 37° C. in a water bath for 10 min. and then assessed for odor intensity, organoleptically.

(b) 1 ml of each of the three samples was incubated at 37° C. and 0.1 ml of formula 78K was added into each sample and mixed well every 10 min. The odor and pH were tested until the foot odor disappeared. A negative control was performed at the same time. The experiment was repeated with test formula 78 L.

Figure 20:
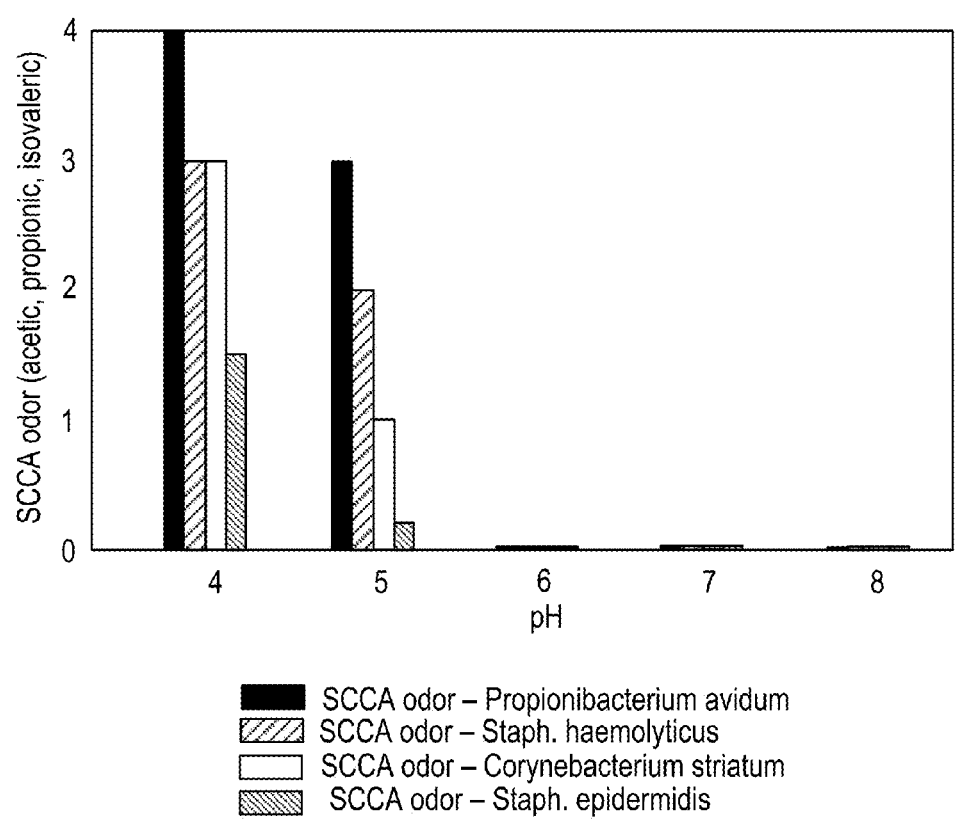
FIG. 20 is a graph showing the relation between SCCA odor and pH when either 25% (v/v) *Propionibacterium avidum*, 25% (v/v) *Staphylococcus haemolyticus*, 25% (v/v) *Corynebacterium striatum* or 25% (v/v) *Staphylococcus epidermidis* was incubated at 37° C. for 4 hours.

Results (i) Experiment 1:

*C. striatum, Staph. haemolyticus, Staph. epidermidis* and *P. avidum*, at 25% (v/v), were each combined and incubated in a water bath at 37° C. for 4 hours. Mild to moderate foot odor was found, when *C. striatum* and *Staph. epidermidis* were incubated at 37° C. and at pH 4.0 to 5.0. Moderate to strong foot odor was discovered, when *Staph. haemolyticus* and *P. avidum* were incubated at 37° C. and pH was at 4.0 to 5.0. Very strong odor was detected, when *P. avidum* was incubated at 37° C. between pH 4.0 and 5.0. The foot odor disappeared, when the pH of the bacterial suspension was raised to pH 6.0 or above (FIG. 20).

Figure 21:
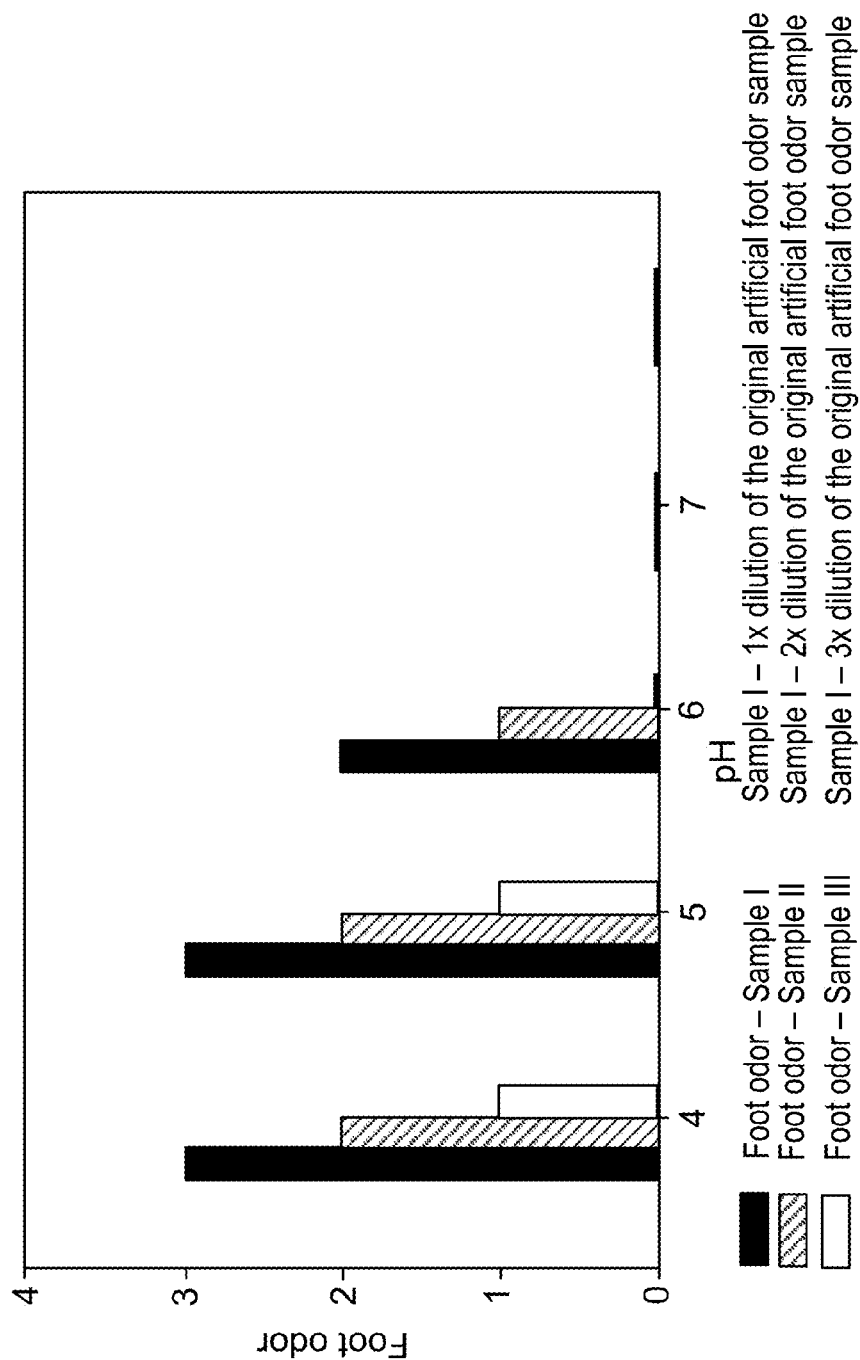
FIG. 21 is a graph showing the foot-web odor in relation to pH when artificial foot odorants were incubated at 37° C. for 4 hours.

(ii) Experiment 2:

(a) The foot odor in Samples I and II were reduced from level 3 to 2 and from level 2 to 1, respectively, when the pH was increased from 4.0 to 6.0. The foot odor of Sample III decreased from level 1 to 0, when the pH was increased from 4.0 to 6.0. In all 3 Samples, foot odor disappeared, when the pH was increased to 6.0 and above (FIG. 21).

Figure 22:
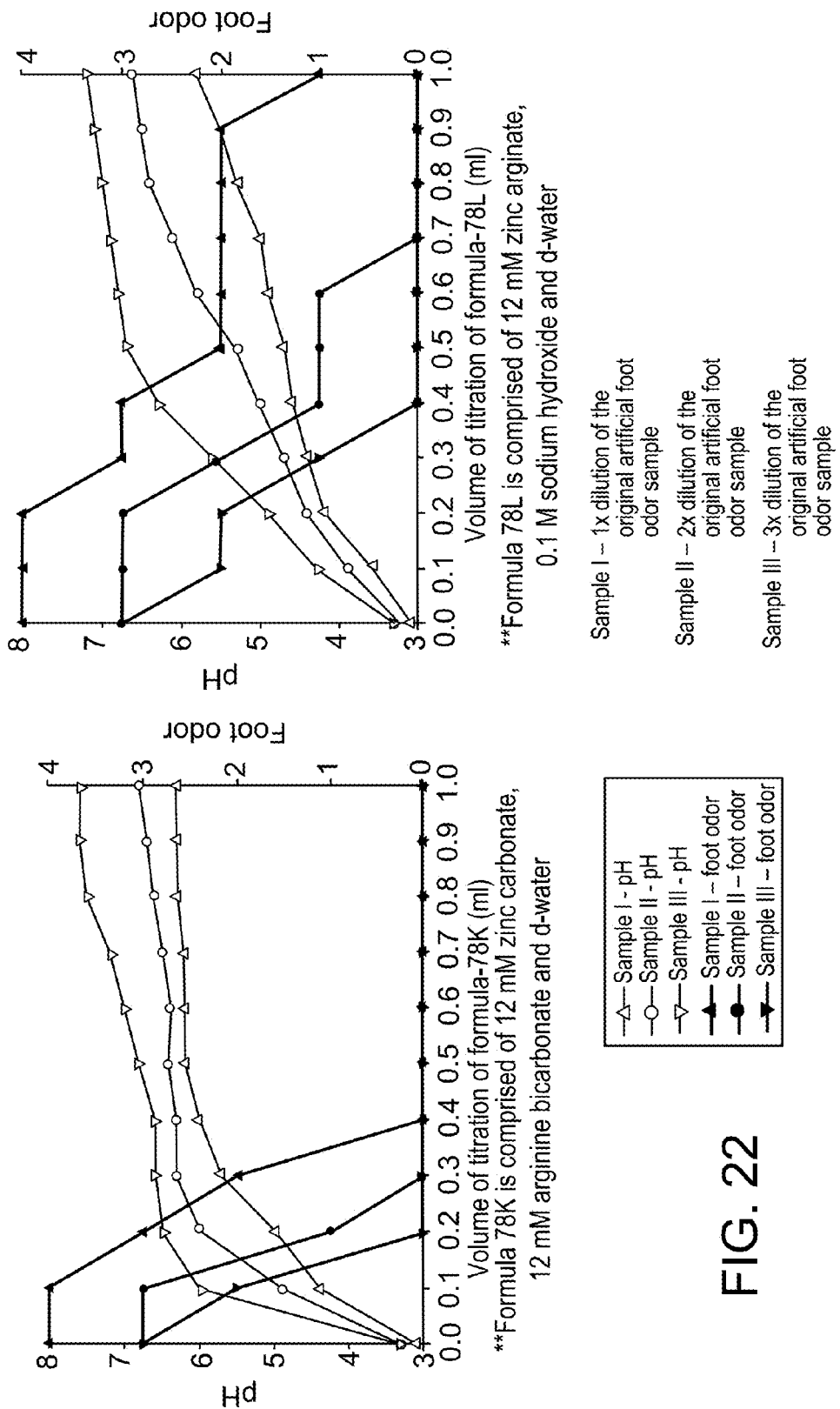
FIG. 22 is a graph showing the foot-web odor and pH in relation to various concentrations of artificial foot odorants 78K (12.0 mM zinc carbonate and 12 mM arginine bicarbonate in water) and 78 L (12.0 mM zinc arginate and 0.1 M sodium hydroxide in water) at 37° C.

(b) When the artificial foot odorants at different concentrations were titrated with deodorant formulae, 78K or 78L, the results showed that foot odor levels gradually decreased, as pH values increased, when titrations were performed in all 3 samples. The foot odor levels decreased from very strong to mild, as pH levels increased from 3.0 to 6.0. As before, the odor disappeared, when the pH of the samples were raised to 6.0 and above. The titration volumes required with formula 78K were less than those with 78L (FIG. 22).

The overall results in these experiments indicated that the intensity of the foot odor smell was strong, when the pH was between 4.0 and 5.0, mild when the pH was between 5.0 and 6.0 and disappeared, when the pH was above 6.0. This is consistent with malodorants that are short chain fatty acids.

Example IV

Growth of *C. striatum* and *Staph. epidermidis* when One or the Other or a Mixture of the Two Bacteria were Incubated in the Presence of (i) Cysteine, (ii) Isoleucine, Leucine, Phenylalanine and (iii) Zinc Carbonate with and without Arginine Bicarbonate at 37° C. For 72 hours Our preliminary experiments showed that cysteine, isoleucine and leucine are the main substrates that produce malodor, when degraded by the axillary microbiome. *C. striatum* is the main axillary micro-organism involved. *Staph. epidermidis* is a major member of the axillary microbiome but is not, or at best is a slight malodor producer. Zinc carbonate together with arginine bicarbonate (ABZC), or zinc carbonate with zinc bicarbonate, are elements that act to inhibit the several odorants involved in axillary malodor. The following procedures have to be kept and manipulated carefully under aseptic conditions.

Materials and Methods

Preparation of Pure Cultures of Micro-organisms

Pure cultures of *C. striatum* and *Staph. epidermidis* were prepared as described above. The bacterial sediments produced upon centrifugation and decantation of the supernatants were stirred and made into a uniform suspension. *C. striatum* and *Staph. epidermidis* were mixed with each of *C. striatum* and *Staph. epidermidis* at 25% (v/v).

Preparation of the Various Substrates Needed for the Tests.

Aqueous solutions of arginine bicarbonate (10 ml of 72 mM) and zinc carbonate (10 ml of 72 mM), were dissolved (partially) in water and the following amino acids: cysteine, isoleucine and leucine (10 ml of 72 mM) along with phenylalanine (10 ml of 144 mM) were prepared from their corresponding stock solutions.

Zinc carbonate was autoclaved and suspended in sterile distilled water. All other stock solutions were sterilized by microbial filtration (Nylon, Sterile filter, pore size 0.20 µM, Fisher Scientific, Fairlawn, N.J. USA).

Preparation of BHI Agar Plates

Difco BHI agar was poured into petri dish plates under sterile conditions and pre-incubated at 37° C. for 24 hours before use to ensure sterility.

Experimental Procedures

Preparation of Samples for Testing

The experimental and negative control samples were prepared as follows:

growth was regularly checked. This was the initial test before the incubation was started.

Four successive diluted samples were selected and grown to proper densities of bacterial colonies on the agar plates; for example, $10^4$ to $10^7$ were appropriate dilutions for all samples in the instant experiment. Incubation of all samples (experimental and control) were continued at 37° C. for 24, 48 or 72 hours; 100 µl of each sample were taken and chosen at 4 consequent dilutions and inoculated on BHI agar plates for incubation for 24, 48 and 72 hours, respectively. Plating on BHI agar plates and incubation at 37° C. for 24 to 48 hours were carried out and bacterial growth on the BHI agar plates were checked.

The number of bacterial colonies on each plate was assessed. The plates inoculated with the mixture of *C. striatum* and *Staph. epidermidis* (i.e., Samples I and IV in the Table of Media compositions above) were counted and the number of colonies of *C. striatum* and *Staph. epidermidis* were determined from the photos of the plates.

Results

The number of colonies of *C. striatum*, *Staph. epidermidis* and a mixture of *C. striatum* and *Staph. epidermidis* decreased gradually during incubation in their respective media at 37° C. for 72 hours. The colonies of bacteria incubated in the media without arginine bicarbonate

TABLE 4.1

| | | Experimental samples | | | | | Negative control | | |
|---|---|---|---|---|---|---|---|---|---|
| | | I | II | III | IV | V | VI | 1 | 2 | 3 |
| Composition | | Natural pH (8.0-8.5) | | | Natural pH (6.5-7.0) | | | Natural pH (6.5 to 7.0) | | |
| a.a. | Cys 72 mM | 0.225 | 0.225 | 0.225 | 0.225 | 0.225 | 0.225 | — | — | — |
| | Ieu 72 mM | 0.225 | 0.225 | 0.225 | 0.225 | 0.225 | 0.225 | — | — | — |
| | Ileu 72 mM | 0.225 | 0.225 | 0.225 | 0.225 | 0.225 | 0.225 | — | — | — |
| | Phe 144 mM | 0.225 | 0.225 | 0.225 | 0.225 | 0.225 | 0.225 | — | — | — |
| | Zinc carbonate 72 mM | 0.450 | 0.450 | 0.450 | 0.450 | 0.450 | 0.450 | — | — | — |
| | Arg. bicarbonate 72 mM | 0.450 | 0.450 | 0.450 | — | — | — | — | — | — |
| Bacteria | *Staph. epidermidis* 25% | 0.450 | — | 0.900 | 0.450 | — | 0.900 | 0.450 | — | 0.900 |
| | *C. striatum* 25% | 0.450 | 0.900 | — | 0.450 | 0.900 | — | 0.450 | 0.900 | — |
| | D-water | — | — | — | 0.450 | 0.450 | 0.450 | 1.800 | 1.800 | 1.800 |
| Total volume (ml) | | 2.700 | 2.700 | 2.700 | 2.700 | 2.700 | 2.700 | 2.700 | 2.700 | 2.700 | a.a., amino acid

The final concentrations of each ingredient in the samples were zinc carbonate at 12 mM, arginine bicarbonate at 12 mM, cysteine at 6 mM, isoleucine at 6 mM, leucine at 6 mM, phenylalanine at 12 mM. The final concentrations of the bacteria, *C. striatum* and *Staph. epidermidis* were each 8.3% (v/v) and the mixture of *C. striatum* and *Staph. epidermidis* were 4.15% (v/v) each.

Figure 23:
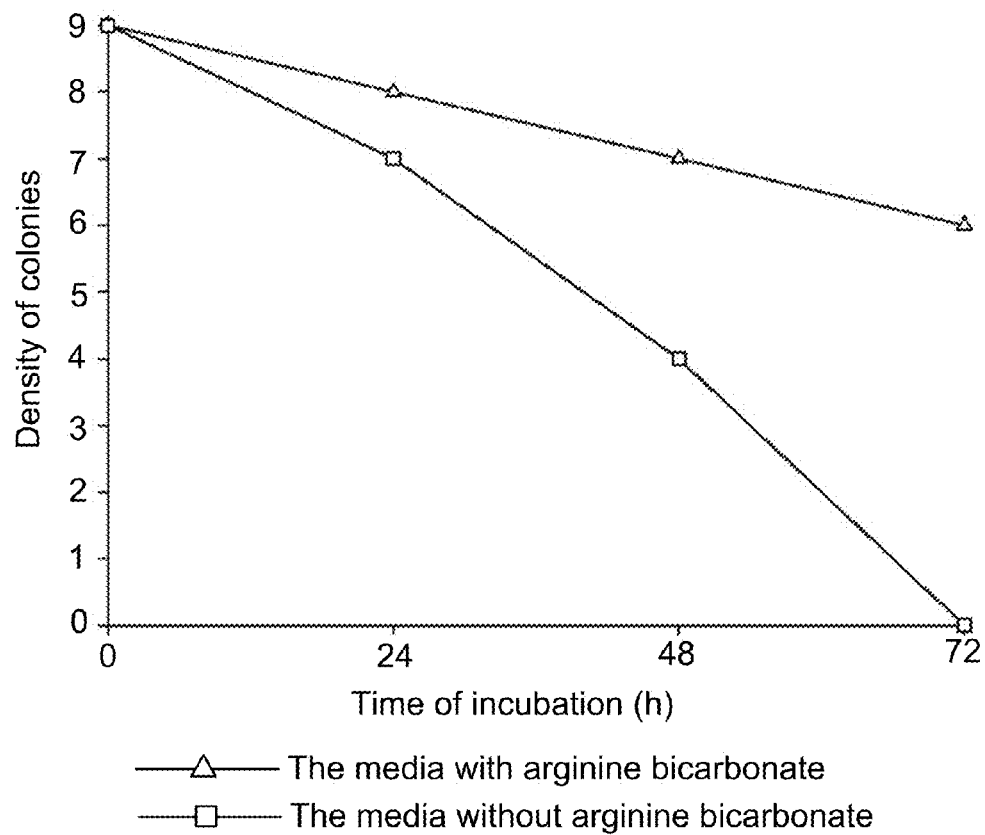
Figure 24:
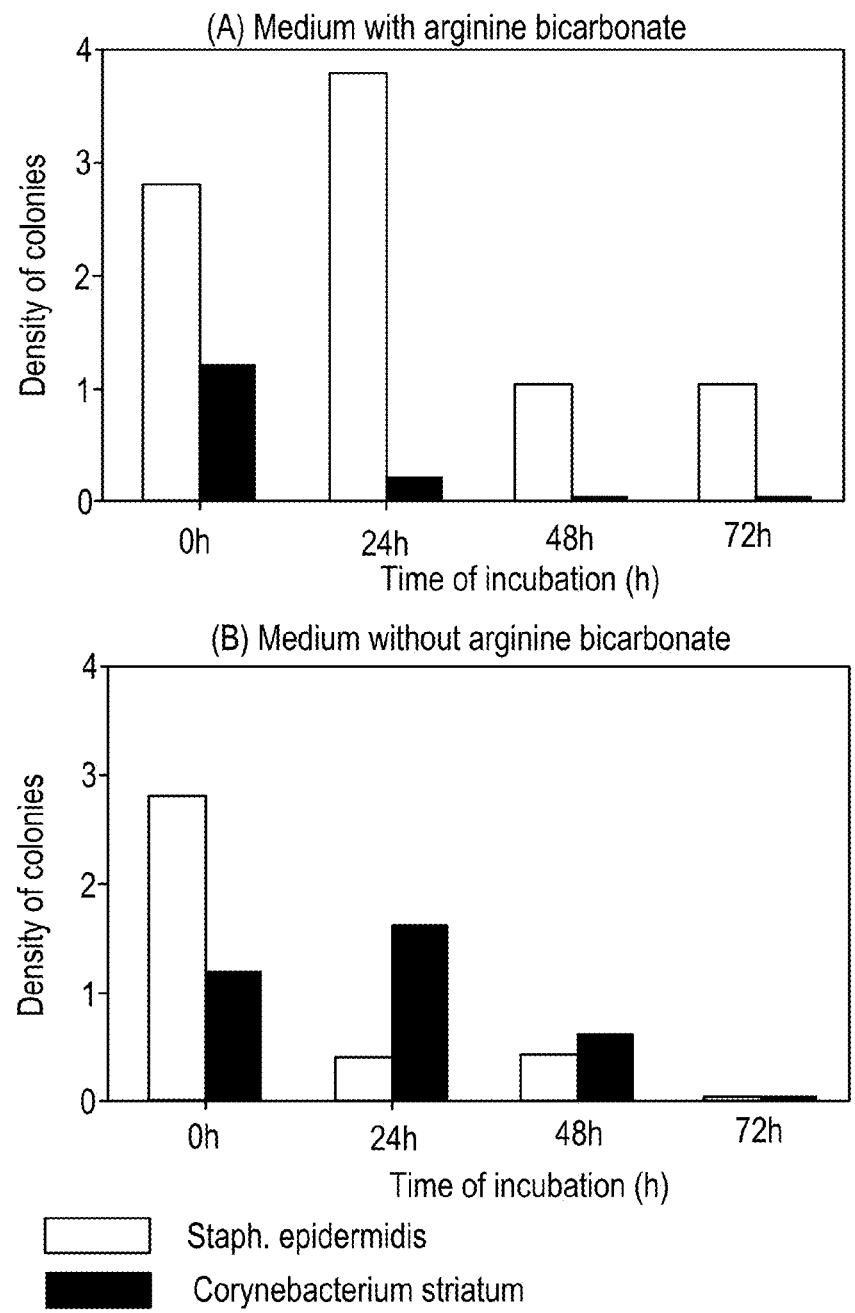
Figure 25:
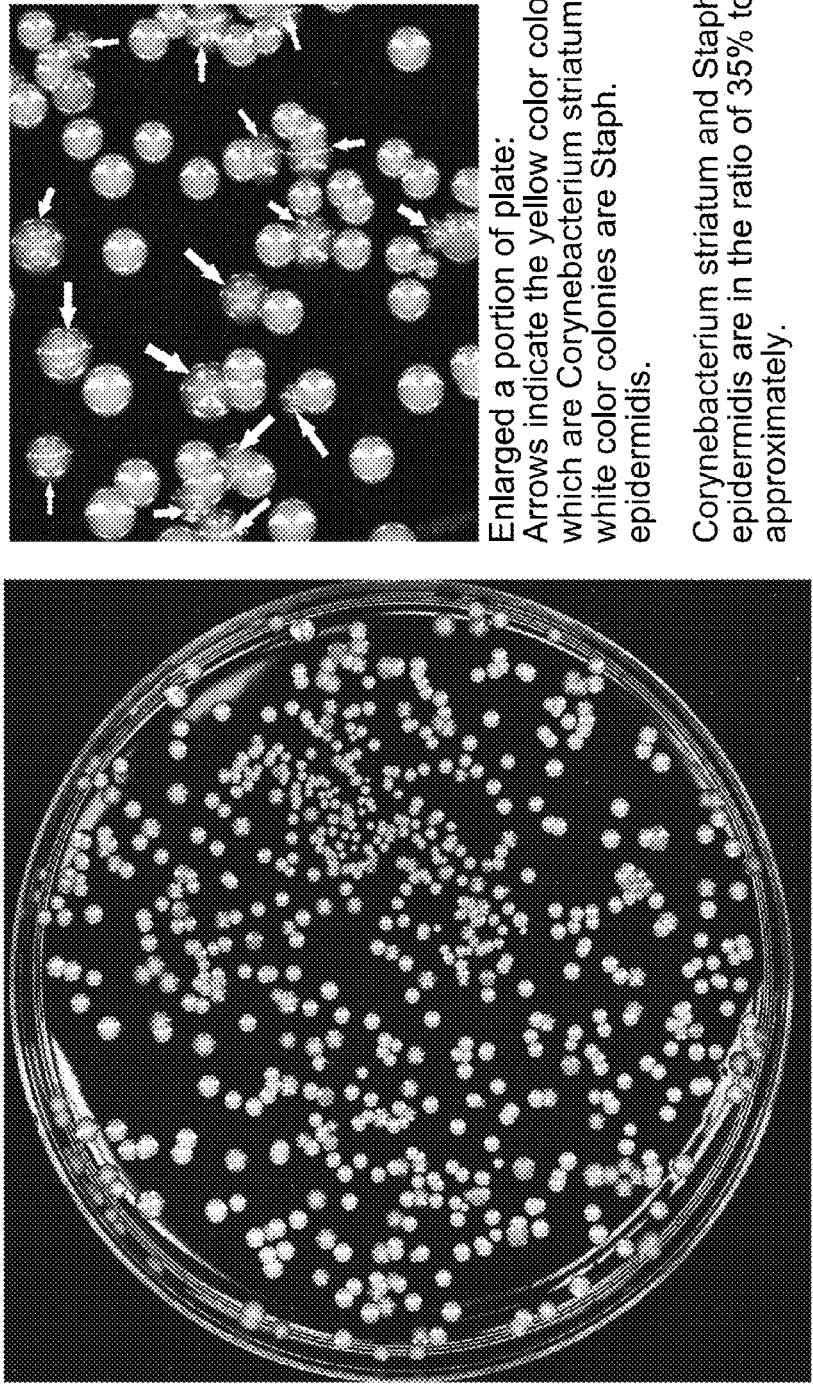
Figure 26:
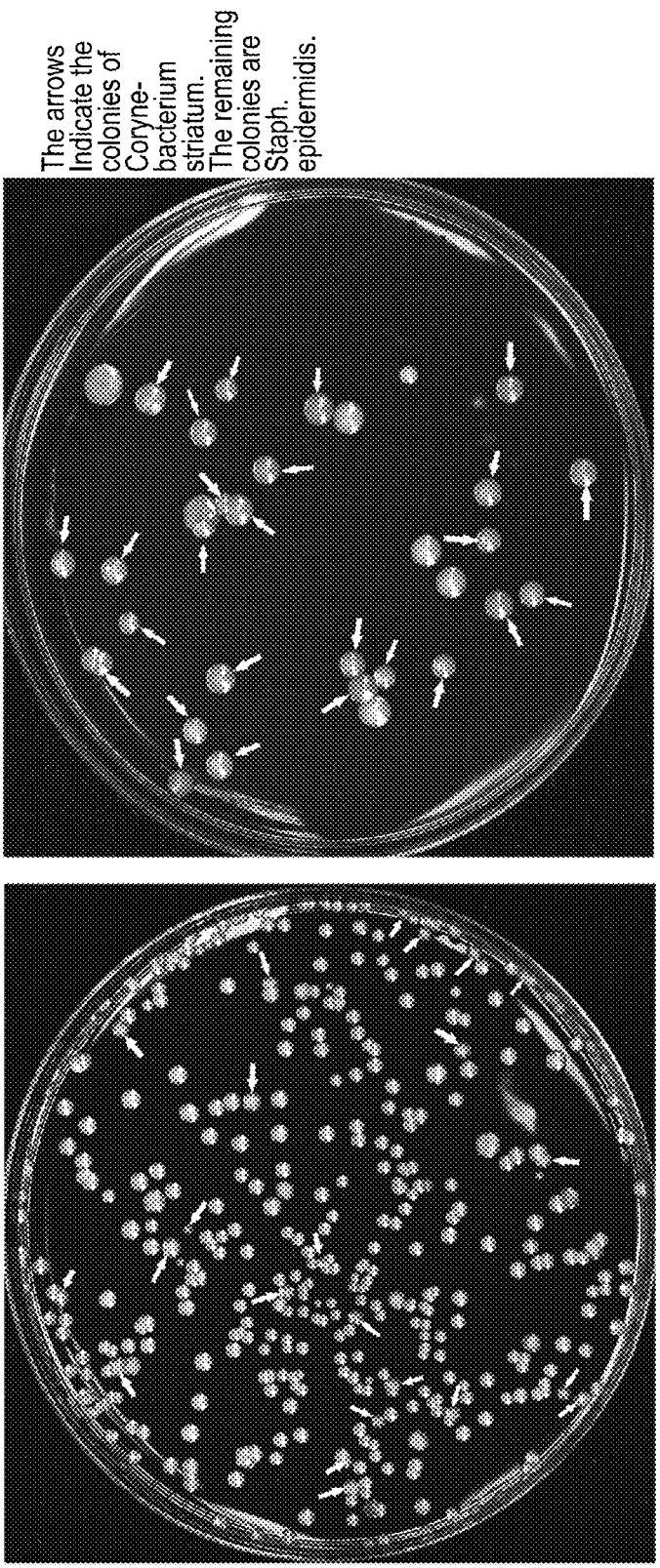
Figure 27:
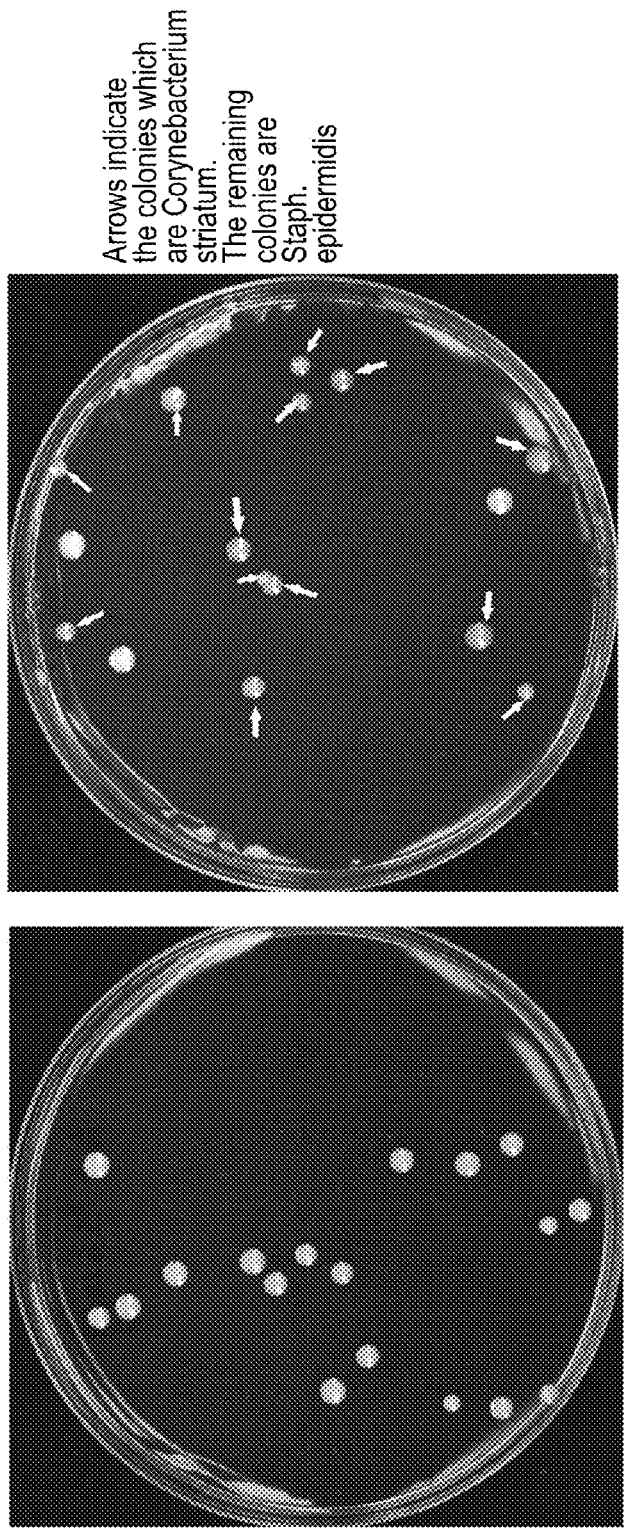

Serial dilution of each of the samples between $10^0$ and $10^{10}$ was made. An aliquot of 100 µl from each $10^0$ to $10^{10}$ dilution was inoculated onto BHI agar plates. The plates were then incubated at 37° C. for 24-48 hours. Bacterial decreased sooner than those incubated in the media with arginine bicarbonate (FIGS. 23 and 24).

The ratio of *C. striatum* and *Staph. epidermidis* in the mixtures changed significantly. *Staph. epidermidis* increased to 90% in 24 hours from 65% at 0 hours. Colonies of *Staph. epidermidis* discovered were at 48 and 72 hours, when the mixture was incubated in media with arginine bicarbonate. In contrast, the number of colonies of *Staph. epidermidis* decreased to about 10-20% in 24 hours from 65% at 0 hours. Only colonies of *Staph. epidermidis* were discovered at 48 and 72 hours, when the mixtures were incubated in the media with arginine bicarbonate (FIGS. 24 and 25-28).

Example V

Bacteriostatic Susceptibility of C. striatum and Staph. epidermidis to Several Deodorant Formulae Measured by the Kirby-Bauer Disk Test Method C. striatum and Staph. epidermidis are among the most prevalent bacteria that comprise the human cutaneous microbiota. Numerous studies have indicated that C. striatum is a less than desirable entity, whereas Staph. epidermidis is a commensal that is more commensurate with skin health. The purpose of this segment was to examine whether formulations arising out of the studies reported in the prior sections that favor the growth and metabolism of Staph. epidermidis as a desirable skin entity that can inhibit the growth of C. striatum, a less desirable entity, and do so when both microorganisms are present initially at the same levels. In this regard, an adaptation of the Kirby-Bauer disk diffusion susceptibility test appeared to be relevant for such determination.

This test was originally developed to determine the sensitivity or resistance of pathogenic aerobic and facultative anaerobic bacteria to various antimicrobial compounds alone and in combination (Bauer and Kirby, 1966). Here we have grown less than desirable C. striatum and highly desirable Staph. epidermidis, alone and in combination, under a variety of substrate conditions to determine, if the latter micro-organism could be selected over C. striatum and thereby be used as a means of reducing the presence of less desirable odor-producing C. striatum.

Materials and Methods

Compositions indicated as possible suppressants of C. striatum and/or enhancers of Staph. epidermidis were based on the prior studies above and for convenience of presentation were categorized as possible active test ingredients and then formulae and mixtures in which they were tested. Accordingly, the total number of compositions tested was eight. Careful attention was paid to sterility throughout in the preparation and handling of the compounds and compositions utilized herein.

(a) Active Test Ingredients and their Sterilization
  (i) arginine bicarbonate in aqueous solutions; 1% and 5% (w/v).
  (ii) zinc carbonate and a related molecule, zinc glycinate in aqueous suspensions at 1%, 3% and 5% (w/v) were tested.

Because of poor solubilities, zinc carbonate and zinc glycinate were each autoclaved as powders before being suspended in sterile distilled water. Sterile solutions of the other ingredients employed herein were prepared by syringe filtration.

(b) Formulae
  (i) 1% zinc carbonate (w/v) and 5% arginine bicarbonate (w/v): prepared first as 2% zinc carbonate and 10% arginine bicarbonate, were each sterilized and then mixed in equal volumes before use.
  (ii) 5% zinc carbonate and 5% arginine bicarbonate: prepared as 10% zinc carbonate and 10% arginine bicarbonate and then mixed in equal volumes.
  (iii) 1% zinc glycinate and 5% arginine bicarbonate: prepared as 2% zinc glycinate and 10% arginine bicarbonate and then mixed in equal volumes.
  (iv) 5% zinc glycinate and 5% arginine bicarbonate: prepared as 10% zinc glycinate and 10% arginine bicarbonate, and then mixed in equal volumes.

Each of these formulae were prepared at 4 different concentrations: original as in (b), and 1.5, 2.5 and 7.5 times the original concentration. Again, all formulae were prepared under aseptic conditions. All solutions were sterilized by syringe filtering, except for zinc carbonate and zinc glycinate, which were autoclaved.

(c) Mixtures
  (i) Mixture A—cysteine, iso-leucine and leucine (the CIL amino acids) each at 6 mM; 12 mM phenylalanine; plus 12 mM zinc carbonate and 12 mM arginine bicarbonate.
  (ii) Mixture B—CIL amino acids, each at 6 mM; 12 mM phenylalanine; plus 12 mM zinc glycinate and 12 mM arginine bicarbonate.

TABLE 5.1

Compositions of mixtures A and B

| | | Mixture A | | Mixture B | |
|---|---|---|---|---|---|
| | | Concentration | | | |
| | | original | 7.5 times | original | 7.5 times |
| amino acid | Cysteine (g) | 0.07 | 0.525 | 0.07 | 0.525 |
| | Leucine (g) | 0.08 | 0.60 | 0.08 | 0.60 |
| | Isoleucine (g) | 0.08 | 0.60 | 0.08 | 0.60 |
| | Phenylalanine (g) | 0.20 | 1.50 | 0.20 | 1.50 |
| Zinc carbonate basic (g) | | 0.66 | 4.95 | — | — |
| Arginine bicarbonate (g) | | 0.36 | 2.70 | 0.36 | 2.70 |
| Zinc glycinate (g) | | — | — | 0.28 | 2.10 |
| D-water (ml) | | 98.55 | 89.125 | 98.93 | 91.975 |
| Total volume (ml) | | 100.00 | 100.00 | 100.00 | 100.00 |

To make compositions 1.5 times the original concentration listed above, formulae 7.5 times the original concentrations were diluted a factor of 5 with sterile distilled water. To make compositions 2.5 times the original concentration listed above, formulae 7.5 times the original concentrations were diluted three-fold with sterile distilled water. To summarize: a total of 3 ingredients, 2 formulae and 2 mixtures were tested. A total of 20 disks were prepared for tests of susceptibility to each bacterial sample and these are outlined in Table 5.2 below:

TABLE 5.2

Ingredients, formulae and mixtures examined

| Ingredients | | | | | | | Formulae | |
|---|---|---|---|---|---|---|---|---|
| | | | | | | | Formula I - Mixture of 5% | Formula II - Mixture of 5% |
| Zinc glycinate (%) | | | Zinc carbonate (%) | | | Arginine bicarbonate (%) | arg. bicarbonate & 1% zinc carbonate | arg. bicarbonate & 1% zinc glycinate |
| 5 | 3 | 1 | 5 | 3 | 1 | 5 | 1 | 5% | 1% | 5% | 1% |

| Mixture I Cys, Leu, Ileu, Phe, Zinc carbonate and Arginine bicarbonate | | | | Mixture II Cys, Leu, Ileu, Phe, Zinc glycinate and Arginine bicarbonate | | | |
|---|---|---|---|---|---|---|---|
| 7.5X | 2.5X | 1.5X | Original | 7.5X | 2.5X | 1.5X | Original |

X, times

Methods and Materials Involved
  (i) Sterile filter paper disks; 12.7 mm (diameter); Blood BHI agar plates (Fisher Scientific, Springfield, N.J. USA); glass rod bars and turning table for inoculation of bacteria onto media plates.

(ii) Bacterial suspensions of *C. striatum* (ATCC 43751) and *Staph. epidermidis* (ATCC 12228) were prepared for plating on medium plates. Each was cultured in BHI broth.
(iii) Prepared 25% bacterial suspensions of each pure culture in sterile D-water.
(iv) Bacterial pellets that were broken up as fine as possible. A TB syringe with a 25-27 G sterile needle was used to help break up the remains of any pellets. The uniformity of bacterial suspensions was checked microscopically.
(v) Suspensions were incubated in a 37° C. water bath for an hour to reduce any stored substrates produced during growth in culture. The pH of each suspension was then measured and recorded.
(vi) 8.3% (VAT) bacterial suspensions of *Staph. epidermidis* and *C. striatum* by diluting 25% bacterial suspensions of each threefold with sterile D-water.
(vii) Final bacterial samples for plating were prepared by diluting each 8.3% (VAT) bacterial suspension by $10^4$ with sterile D-water, before storing at 4° C. for subsequent plating.

Plating Procedures

Five bacterial samples of *C. striatum* and *Staph. epidermidis* were plated on Blood BHI agar and CHROMagar plates, respectively.

100 µl of each bacterial sample was inoculated on Blood BHI agar plates by using sterile glass bars and a turning table to facilitate each bacterial sample being spread evenly on each of the agar plates.

Each spread bacterial suspension was allowed to dry on inoculated plates for five minutes.

Paper disks were immersed, respectively, with the above 3 ingredients, 2 formulae and 2 mixtures; absorptions were saturated.

Four disks were placed on each plate with sterile forceps.

Incubated plates within 15 minutes after applying the disks to ensure test was under standardized conditions, where diffusion of the ingredients and formulae and bacterial growth commence at approximately the same time. Plates were incubated at 37° C. for 24 hours.

Interpretation of Results

Each strain was determined as resistant, intermediate, or susceptible to the ingredients, formulae and mixtures tested. After 24 hours of incubation at 37° C., the diameter of the zone of growth inhibition around each disk was measured to the nearest whole mm. Plates were carefully examined for well-developed colonies within the zone of inhibition.

Results

The viabilities of *Staph. epidermidis* and *C. striatum* upon exposure to the various ingredients, formulae and mixtures shown in Table 5.3 are elaborated upon below.

TABLE 5.3

Susceptibility of *Staph. epidermidis* (SE) and *C. striatum* (CS) to the individual ingredients, formulae and mixtures involved herein in their viability determined by the Kirby-Bauer disk test

| | Ingredients, Formulae and Mixtures | Concentrations and pH | *Staph. epidermidis* (SE) 8.3% diluted to $10^4$ – 0.1 ml | *C. striatum* (CS) 8.3% diluted to $10^4$ – 0.1 ml |
|---|---|---|---|---|
| | | | Blood BHI agar plate | |
| Ingredients | Zinc carbonate | 5% (pH 7.5) | — | ++ (p) 15 mm |
| | | 3% (pH 7.5) | — | + (p) 14 mm |
| | | 1% (pH 7.2) | — | ± (p) |
| | Zinc glycinate | 5% (pH 6.6) | — | ++ (p) 17 mm |
| | | 3% (pH 6.6) | — | + (p) 14 mm |
| | | 1% (pH 6.6) | — | — |
| | Arginine bicarbonate | 5% (pH 8.4) | — | — |
| | | 1% (pH 8.4) | — | — |
| Formulae | Formula I - 5% arginine bicarbonate and zinc carbonate | 5% (pH 8.4) | — | ++ (p) 15 mm |
| | | 1% (pH 8.4) | — | ± (p) |
| | Formula II - 5% arginine bicarbonate and zinc glycinate | 5% (pH 8.3) | ++ (p) 17 mm | ++ (p) 18 mm |
| | | 1% (pH 8.3) | — | — |
| Mixtures | (A). Cys, Leu, Ileu (6 mM each), Phe, $ZnCO_3$ and $Arg(HCO_3)_2$ (12 mM each) | 7.5 times of org. (pH 8.1) | ± (p) | + (p) 16 mm |
| | | 2.5 times of org. (pH 8.1) | — | ++ (p) 16 mm |
| | | 1.5 times of org. (pH 8.3) | — | + (p) 14 mm |
| | | Org. (pH 8.3) | — | — |
| | (B). Cys, Leu, Ileu (6 mM each), Phe, Zn glycinate and $Arg(HCO_3)_2$ (12 mM each) | 7.5 times of org. (pH 7.6) | ++ (p) 18 mm | ++ (p) 17 mm |
| | | 2.5 times of org. (pH 7.7) | ++ (p) 15 mm | ++ (p) 15 mm |
| | | 1.5 times of org. (pH 7.6) | — | — |
| | | Org. (pH 7.7) | — | — |

The diameter of a paper disk: 12.7 mm; (p): partial inhibition; (c): complete inhibition; (—) to (++++): Intensity of inhibition of the growth of bacteria: (—) no inhibition, (±) suspicious inhibition, (+) the diameter of inhibition <15 mm, (++) the diameter of inhibition 15-20 mm, (+++) the diameter of inhibition 21-30 mm, (++++) the diameter of inhibition >30 mm; pH of mixture of Cys, Leu, Ileu (6 mM/each) and Phe, zinc glycinate (12 mM/each), without arginine bicarbonate at the concentrations of original, 1.5 times, 2.5 times and 7.5 times the original: 5.4-5.5.

(a) Viability of *Staph. epidermidis* and *C. striatum* upon exposure to zinc carbonate and zinc glycinate

*C. striatum* showed viability loss (i.e. 14 and 15 mm rings in partial inhibition) when exposed to low or moderate (3% and 5%) zinc carbonate levels or to similar levels of zinc glycinate (i.e. 14 and 17 mm rings in partial inhibition) on Blood BHI agar plates. *C. striatum* was not sensitive to either 1% zinc carbonate or 1% zinc glycinate on similar Blood BHI agar plates. Importantly, *Staph. epidermidis* was not sensitive to viability loss with exposure to either of these two zinc compounds on these agar plates. Also, neither *C. striatum* nor *Staph. epidermidis* was susceptible to arginine bicarbonate upon exposure thereto at either 1% or 5% levels.

(b) Viability of *Staph. epidermidis* and *C. striatum* upon exposure to the following formulae: Formula I—a mixture of arginine bicarbonate and zinc carbonate; Formula II—a mixture of arginine bicarbonate and zinc glycinate.

*C. striatum* was sensitive to both formulae. Formula I—a mixture of 5% arginine bicarbonate and 5% zinc carbonate showed 15 mm rings in partial inhibition and Formula II—a mixture of 5% arginine bicarbonate and 5% zinc glycinate showed 18 mm rings in partial inhibition, and was not sensitive to 1% of either Formula I or Formula II on Blood BHI agar. *Staph. epidermidis* was not at all sensitive at either 1% or 5% with both Formula I (pH 8.4), the mixture of arginine bicarbonate and zinc carbonate; whereas it was moderately sensitive to Formula II (pH 8.3)—the mixture of 5% arginine bicarbonate and 5% zinc glycinate (17 mm rings in partial inhibition) on Blood BHI agar plates but was not sensitive to 1% of Formula II.

(c) Viability of *Staph. epidermidis* and *C. striatum* when exposed to the following mixtures.

*C. striatum* was sensitive to both mixture A (CIL amino acids, phenylalanine, zinc carbonate and arginine bicarbonate) and mixture B (CIL amino acids, phenylalanine, zinc glycinate and arginine bicarbonate) at the concentrations of 7.5 times and 2.5 times originals (16 mm and 15-17 mm rings in partial inhibition, respectively). Low sensitivity to Mixture A was seen at a concentration 1.5 times that of the original (14 mm rings in partial inhibition). It was not sensitive to Mixture A at its original concentration nor to Mixture B in the concentrations of the original and 1.5 times the original. *Staph. epidermidis* was resistant to all concentrations (i.e. the original concentration and to 7.5, 2.5, and 1.5 times the original concentration) of Mixture A, whereas it was moderately sensitive to 7.5 and 2.5 times the original concentration of Mixture B (18 mm and 15 mm rings in partial inhibition, respectively).

The overall results indicated that: *C. striatum* was sensitive to both 3% and 5% zinc carbonate (pH 7.5) and 3% and 5% zinc glycinate (pH 6.6), low and moderate on Blood BHI agar plates. *Staph. epidermidis* was not sensitive to either of the above two zinc compounds. *C. striatum* was (i) sensitive to 5% Formulae I and II (both at pH 8.3-8.4), Mixtures A and B moderately at concentrations of 7.5, 2.5 times the original (pH 8.1 and 7.6-7.7, respectively) (ii) showed low sensitivity of 1.5 times that of original Mixture A, and (iii) whereas *Staph. epidermidis* was not sensitive to Formula I and Mixture A at any concentration (pH 8.1-8.3). (iv) in contrast, it was moderately sensitive to both 5% Formula II (pH 8.3) and Mixture B in the concentrations of 7.5, and 2.5 times the original (pH 7.6-7.7).

The different susceptibilities of *Staph. epidermidis* to Formula I, Mixture A and Formula II Mixture B, showed that the growth of *Staph. epidermidis* was inhibited by Formula II and Mixture B but not Formula I and Mixture A. The inhibition appeared, when the pH rose above 7.7, where the solubility of zinc glycinate increases.

The solubility of zinc glycinate was very limited in water and the pH was low (6.6) in 1.0-5.0% water suspensions. The pH was only 5.4, when zinc arginate suspension was incubated with the CIL amino acids, and phenylalanine SCCA would not be de-ionized at this acidic pH.

The present invention is not limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description. Patents, patent applications, publications, product descriptions, and protocols are cited throughout this application, the disclosures of which are incorporated herein by reference in their entireties for all purposes.

REFERENCES

1. Centers for Disease Control and Prevention: Public health dispatch: outbreaks of community-associated methicillin-resistant *Staphylococcus aureus* skin infections—Los Angeles County, California, 2002-2003. MMWR Morb. Mortal. Wkly. Rep., 52:88, 2003.
2. Chen, A. E., Goldstein, M., Carroll, K., Song, X., Perl, T. M., Siberry, G. K.: Evolving epidemiology of pediatric *Staphylococcus aureus* cutaneous infections in a Baltimore hospital. Pediatr. Emerg. Care, 22:717-723, 2006.
3. David, M. Z., Daum, R. S.: Community-associated methicillin-resistant *Staphylococcus aureus*: epidemiology and clinical consequences of an emerging epidemic. Clin. Microbiol. Review, 23 (3):616-87, 2010.
4. Denepitiya, L., Kleinberg, I.: A comparison of the acid-base and aciduric properties of various serotypes of the bacterium *Streptococcus* mutants associated with dental plague. Arch. Oral Biol., 29:385-393, 1984.
5. Denepitiya, L., Kleinberg, I.: A comparison of the microbial compositions of pooled human dental Plaque and salivary sediment. Arch. Oral Biol., 27:739-845, 1982.
6. Emter, R., Natsch, A.: The sequential action of a dipeptidase and a β-lyase is required for the release of the human body odorant 3-methyl-3-sulfanylhexan-1-ol from a secreted cys-gly-(s) conjugate by Corynebacteria. J. Biol. Chem., 283 (30):20645-20652, 2008.
7. Frank, D. N., Feazel, L. M., Bessesen, M. T., Price, C. S., Janoff, E. N., Pace, N. R.: The human nasal microbiota and *Staphylococcus aureus* carriage. PLOS ONE 5 (5): e10598, 2010.
8. French, G. L.: Methods for screening for methicillin-resistant *Staphylococcus aureus* carriage. Clin. Microbiol. Infect. 15 (Suppl. 7):10-16, 2009.
9. Gallo, R. L., Nakatsuji, T.: Firmocidin, an antimicrobial molecule produced by *Staphylococcus epidermidis*. U.S. Patent Application Publication 2013/0331384 A1.
10. Han, Z., Lautenbach, E., Fishman, N., Nachamkin, I.: Evaluation of mannitol salt agar, CHROMagar *Staph aureus* and CHROMagar MRSA for detection of methicillin-resistant *Staphylococcus aureus* from nasal swab specimens. J. Med. Microbiol., 56 (1):43-46, 2007.

11. Jackman, P. J. H.: Body odor—the role of skin bacteria. Sem. Dermatol., 1 (2):143-148, 1982.
12. Kleinberg, I., Codipilly, D.: Cysteine challenge testing: a powerful tool for examining oral malodour processes and treatments in vivo. Inter. Dental J., 52:221-228, 2002.
13. Kleinberg, I., Codipilly, D.: $H_2S$ generation and Eh reduction in cysteine challenge testing as a means of determining the potential of test products and treatments for inhibiting oral malodor. J. Breath Res., 2:1-9, 2008.
14. Kleinberg, I., Codipilly, D.: Modeling of the oral malodor system and methods of analysis. Quint. Int., 30:357-396, 1999.
15. Klevens, R. M., Morrison, M. A., Nadle, J., Petit, S., Gershman, K., Petit, S., Ray, S., Harrison, L. H., Lynfield, R., Dumyati, G., Townes, J. M., Craig, A. S., Zell, E. R., Fosheim, G. E., McDougal, L. K., Carey, R. B., Fridkin, S. K.: Invasive methicillin-resistant *Staphylococcus aureus* infections in the United States. J. Am. Med. Assoc., 298:1763-1771, 2007.
16. Leyden, J. J., McGinley, K.: Coryneform bacteria. The skin microflora and microbial skin disease. Cambridge Univ. Press, 102-141, 1992.
17. Leyden, J. J., McGonley, K. J., Holzle, E., Labows, J. N., Kligman, A. M.: The microbiology of human axilla and its relationship to axillary odor. J. Inv. Derm., 77:413-416, 1981.
18. Mainous III, A. G., Hueston, W., Everett, C. J., Diaz, V. A.: Nasal Carriage of *Staphylococcus aureus* and Methicillin-Resistant *S aureus* in the United States 2001-2002. Ann. Fam. Med., 4 (2):132-137, 2006.
19. Nakatsuji, T., Nam, S., Fenical, W., Gallo, R. L.: Skin commensal bacteria acts as antimicronial shield: Identification of firmocidin, a novel small-molecule antobiotoc produced by *Staphylococcus epidermidis*. J. Inv. Derm., 132:S114, 2012.
20. Nobel, W. C.: Staphylococci on the skin. The skin microflora and microbial skin disease. Cambridge Univ. Press, 135-152, 1992.
21. Pader, M.: Oral hygiene products and practice. Cosmetic science and technology series. New York, Basel: Marcel Dekker, 6:344-359, 1988.
22. Peacock, S. J., de Silva, I., Lowy, F. D.: What determines nasal carriage of *Staphylococcus aureus*? TRENDS Microbiol., 9 (12):605-610, 2001.
23. Sandham, H. J., Kleinberg, I.: Effect of glucose concentration on carbon dioxide production in a human salivary sediment system. Arch. Oral Biol., 15:1285, 1970.
24. Shehadeh, N., Kligman, A. M.: The bacteria responsible for axillary odor II. J. Invest. Derm., 41:3, 1963.
25. Starkenmann, C., Niclass, Y., Troccaz, M., Clark, A. J.: Identification of the precursor of (S)-3 methyl-3-sulfanylhexan-1-ol, the sulfury malodour of human axilla sweat. Chem Biodivers., 2:705-716, 2005.
26. Taylor, D., Daulby, A., Grimshaw, S., James, G., Mercer, J., Vaziri, S.: Characterization of the microflora of the human axilla. Intern. J. Cosm. Scien., 25:137-145, 2003.
27. Troccaz, M., Starkenmann, C., Niclass, Y., Waal, Mvd., Clark, A. J.: 3 methyl-3-sulfanylhexan-1-ol, as a major descriptor for the human axilla-sweat odour profile. Chem Biodiversity, 1:1022-1035, 2004.
28. Uehara, Y., Nakama, H., Agematsu, K., Uchida, M., Kawakami, Y., Abdul Fattah, A. S. M., Maruchi, N.: Bacterial interference among nasal inhabitants: eradication of *Staphylococcus aureus* from nasal cavities by artificial implantation of *Corynebacterium* sp. J. Hosp. Infect., 44:127-133, 2000.
29. Wertheim, H. L. F., Melles, D. C., Vos, M. C., Leeumen, W. V., Belkum, A. V., Verbrugh, H. A., Nouwen, J. L.: The role of nasal carriage in *Staphylococcus aureus* infection. Lancet Infect. Dis. 5:751-62, 2005.
30. Wijeyeweera, R. L., Kleinberg, I.: Acid-base pH curves in vitro with mixtures of pure cultures of human oral microorganisms. Arch. Oral Biol., 34 (1):55-64, 1989.
31. Zeng, X. N., Leyden, J. J., Lawley, H. J., Sawano, K., Hohara, I., Preti, G.: Analysis of characteristic odors from human male axillae. J. Chem. Ecol., 17 (7):1469-1492, 1991.

What is claimed is:

1. A body odor deodorant composition, comprising:
   a. arginine, or a salt thereof;
   b. a zinc salt;
   c. a buffer sufficient to maintain the pH of said composition at 6.0 or greater upon topical application;
   d. a physiologically-acceptable carrier suitable for topical cutaneous application, said composition provided as a topical formulation selected from the group consisting of soap, powder, roll-on, lotion, cream, stick, sachet, film, patch and ointment; and
   e. phenylalanine.

2. The composition of claim 1, said composition being capable of inhibiting the growth or metabolism of malodor-generating microbiota present in the cutaneous regions of a subpart of the human body.

3. The composition of claim 2, wherein said cutaneous regions comprise the axilla and foot-webs.

4. The composition of claim 2, said composition being capable of inhibiting the generation of hydrogen sulfide by said microbiota.

5. The composition of claim 2, said composition being capable of inhibiting the generation of isovaleric acid by said microbiota.

6. The composition of claim 2, said composition being capable of inhibiting the generation of at least one of acetic acid and propionic acid by said microbiota.

7. The composition of claim 2, said composition being capable of inhibiting the generation of at least one of hydrogen sulfide, acetic acid, propionic acid and isovaleric acid by said microbiota.

8. The composition of claim 1, said composition being capable of inhibiting the growth or metabolism of *Corynebacterium striatum*.

9. The composition of claim 1, wherein said zinc salt is selected from the group consisting of zinc carbonate, zinc bicarbonate, zinc glycinate, zinc acetate, zinc lactate and zinc arginate.

10. The composition of claim 9, wherein said zinc carbonate is present at a concentration of 10% (w/v) or less.

11. The composition of claim 9, wherein said zinc carbonate is present at a concentration of 5% (w/v) or less.

12. The composition of claim 1, wherein said arginine, or a salt thereof is selected from the group consisting of arginine, arginine carbonate and arginine bicarbonate.

13. The composition of claim 12, wherein said arginine bicarbonate is present at a concentration of 10% (w/v) or less.

14. The composition of claim 12, wherein said arginine bicarbonate is present at a concentration of 5% (w/v) or less.

15. The composition of claim 1, wherein said zinc salt is zinc carbonate and said arginine salt is arginine bicarbonate.

16. The composition of claim 1, wherein said composition upon topical application has a pH of at least 7.0.

17. The composition of claim 1, wherein said composition upon topical application has a pH of at least 8.0.

18. The composition of claim 1, wherein said composition upon topical application has a pH of at least 9.0.

19. A composition for altering the bacterial degradation products of perspiration odor, comprising zinc carbonate and arginine bicarbonate, and a physiologically-acceptable carrier suitable for topical application, wherein said composition upon topical application has a pH of 6.0 or greater, said composition provided as a topical formulation selected from the group consisting of soap, powder, roll-on, lotion, cream, stick, sachet, film, patch and ointment.

20. A method for treating malodor, comprising topically applying to a cutaneous region of a subject in need thereof, a composition including an arginine salt; a zinc salt; a physiologically-acceptable carrier suitable for topical body cutaneous application; and phenylalanine, wherein said composition upon topical application has a pH of 6.0 or greater, and said composition provided as a topical formulation selected from the group consisting of soap, powder, roll-on, lotion, cream, stick, sachet, film, patch and ointment.

* * * * *